US006034062A

United States Patent [19]
Thies et al.

[11] Patent Number: 6,034,062
[45] Date of Patent: Mar. 7, 2000

[54] BONE MORPHOGENETIC PROTEIN (BMP)-9 COMPOSITIONS AND THEIR USES

[75] Inventors: R. Scott Thies, Andover; Jeffrey J. Song, Brighton, both of Mass.

[73] Assignee: Genetics Institute, Inc., Cambridge, Mass.

[21] Appl. No.: 08/815,652

[22] Filed: Mar. 13, 1997

[51] Int. Cl.[7] .............................. A61K 38/18; C07K 14/51
[52] U.S. Cl. ............................ 514/12; 530/350; 530/399; 930/120
[58] Field of Search .................................... 530/350, 399; 930/120; 514/12

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,619,989 | 10/1986 | Urist | 530/417 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,795,804 | 1/1989 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck | 435/69.4 |
| 4,968,590 | 11/1990 | Kuberasampath et al. | 530/326 |
| 5,011,691 | 4/1991 | Oppermann | 424/423 |
| 5,106,626 | 4/1992 | Parsons et al. | 424/423 |
| 5,108,753 | 4/1992 | Kuberasampath | 424/422 |
| 5,661,007 | 8/1997 | Wozney et al. | 435/69.4 |

FOREIGN PATENT DOCUMENTS

| | | |
|---|---|---|
| 2 017466 | 5/1990 | Canada . |
| 33 6760 | 6/1989 | European Pat. Off. . |
| 4 165 78A2 | 5/1990 | European Pat. Off. . |
| 4 094 72 A1 | 11/1990 | European Pat. Off. . |
| WO 89/09787 | 10/1989 | WIPO . |
| WO 89/09788 | 10/1989 | WIPO . |
| WO 90/03733 | 4/1990 | WIPO . |
| WO 91/02744 | 3/1991 | WIPO . |
| WO 91/05802 | 5/1991 | WIPO . |
| WO 91/18047 | 11/1991 | WIPO . |
| WO 92/07004 | 4/1992 | WIPO . |
| WO 92/07073 | 4/1992 | WIPO . |
| WO 93/04692 | 3/1993 | WIPO . |
| WO 93/05751 | 4/1993 | WIPO . |
| WO 95/33830 | 12/1995 | WIPO . |

OTHER PUBLICATIONS

Sporn et al. 1988. Peptide growth factors are multifunctional. Nature, vol. 332, pp. 217–219, Mar. 1988.
Baird et al. 1986. Inhibition of endothelial cell proliferation by type–beta transforming growth factor: interactions with acidic and basic fibroblast growth factors. Biochem. Biophys. Res. Commun. vol. 138, pp. 476–482, Jul. 1986.
Roberts et al. 1986. Transforming growth factor type–beta: rapid induction of fibrosis and angiogenesis in vivo and stimulation of collagen formation in vitro. Proc. Natl. Acad. Sci. USA, vol. 83, pp. 4167–4171, Jun. 1986.
Shipley et al. 1986. Reversible inhibition of normal human prokeratinocyte proliferation by type beta transforming growth factor–gorwth inhitor in serum–free medium. Cancer Res., vol. 46, pp. 2068–2071, Apr. 1986.
Beck et al. 1990. Accelerated healing of ulcer wounds in the rabbit ear by recombinant human transforming grrowth–beta 1. Growth Factors, vol. 2, pp. 273–282, Feb. 1990.
Nathan C; Sporn M. Cyokines in context. Journal of Cell Biology, (Jun. 1991 113 (5) 981–986.
Wozney et al. 1988. Novel regulators of bone formation: molecular clones and activities. Science, (Dec. 16, 1988) 242 (4885) 1528–1534.
Wozeny et al, pp. 725–748 in Handbook of Exp. Pharm., vol. 107 (Springer–Verlag, Berlin, 1993).
Wang et al, "Recombinant human bone morphogenetic protein . . . " *PNAS 87*: 2220–2224, Mar. 1990.
Celeste et al "Identification of transforming growth factor & family members . . . ", *PNAS 87*: 9843–9847 (Dec. 1990).
Wozney et al, "Novel Regulation of Bone Formation..." *Science 242*: 1528–1534 (Dec. 1988).
Burt et al, "Evolutionary Grouping of the Transforming Growth Factor–⊖Superfamily", *BBRC 184(2)*: 590–595 (Apr. 1992).
Wozney et al, "Growth factors influencing bone development", *J. Cell Sci. Suppl. 13*: 149–156, 1990.
Wozney, J. M. et al. (1988) "Novel Regulators of Bone Formation Molecular Clones and Activities", *Science*, vol. 242, pp. 1528–1533.
Urist et al., *Science 220*: 680–686 (1983).
Luyten et al., *The Journal of Biological Chemistry 264(23)*:3377–13380 (1989).
Sampath et al., *Proc. Natl Acad. Sci 84*:7109–7113 (1987).
Ozkaynak et al., *The EMBO Journal v. 9 No. 7*:2085–2093 (1990).
Hammonds et al., *Molecular Endocrinology 5*:149–155 (1991).

(List continued on next page.)

Primary Examiner—Elizabeth Kemmerer
Assistant Examiner—David S. Romeo
Attorney, Agent, or Firm—M. C. Mienert; Ellen J. Kapinos

[57] ABSTRACT

Purified Bone Morphogenetic Protein (BMP)-9 proteins and processes for producing them are disclosed. The proteins may be used in the treatment of bone and cartilage defects and in wound healing and related tissue repair, and in hepatic growth and function.

3 Claims, 9 Drawing Sheets

OTHER PUBLICATIONS

Celeste et al., *J. of Bone Mineral Res.* v. 9 suppl. 5136 (1994).

Celeste et al., *Proc. Natl. Acad. Sci.* 87:9843–9847 (1990).

Burt et al., *BBRC* 184(2):590–595 (1992).

Wozney et al., *J. Cell Sci. Suppl.* 13:149–156 (1990).

Wang et al., *Proc. Natl.. Acad. Sci.* 87:220–2224 (1990).

Hebda et al. 1988. Stimulatory effects of transforming growth factor–beta and epidermal growth factor on epidermal cell outgrowth from porcine skin expalnt cultures. J. Invest. Dermatol., vol. 91, pp. 440–445, Nov. 1988.

McDonald et al. 1993. A structural superfamily of growth factors containing a cystine knot motif. Cell, vol. 73, pp. 421–424, May 1993.

Fig. 3
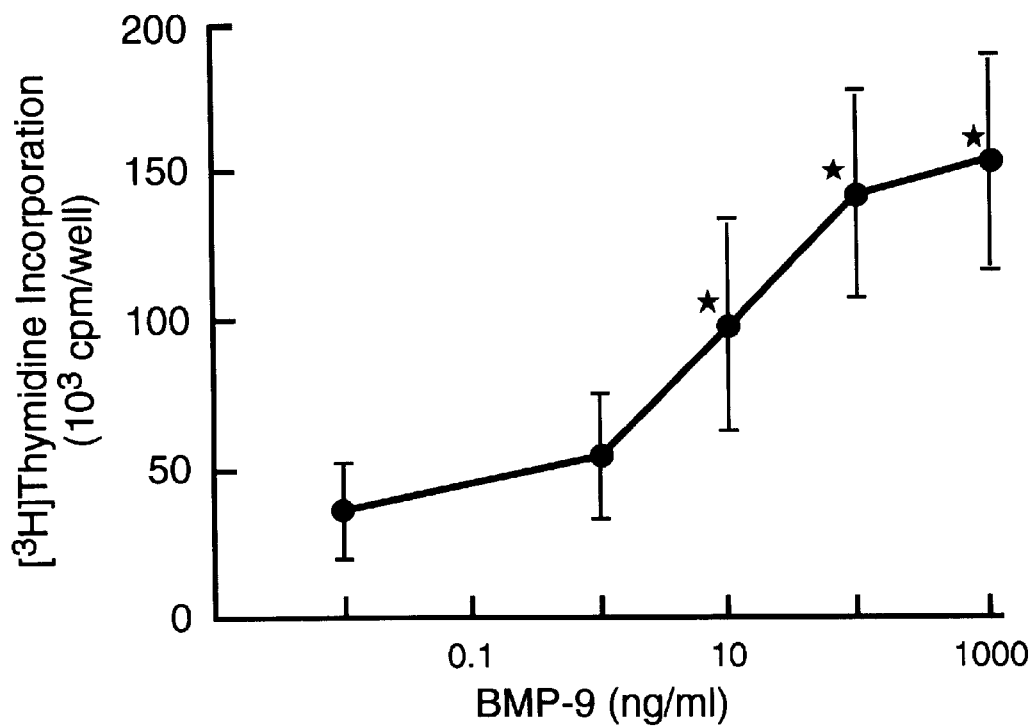
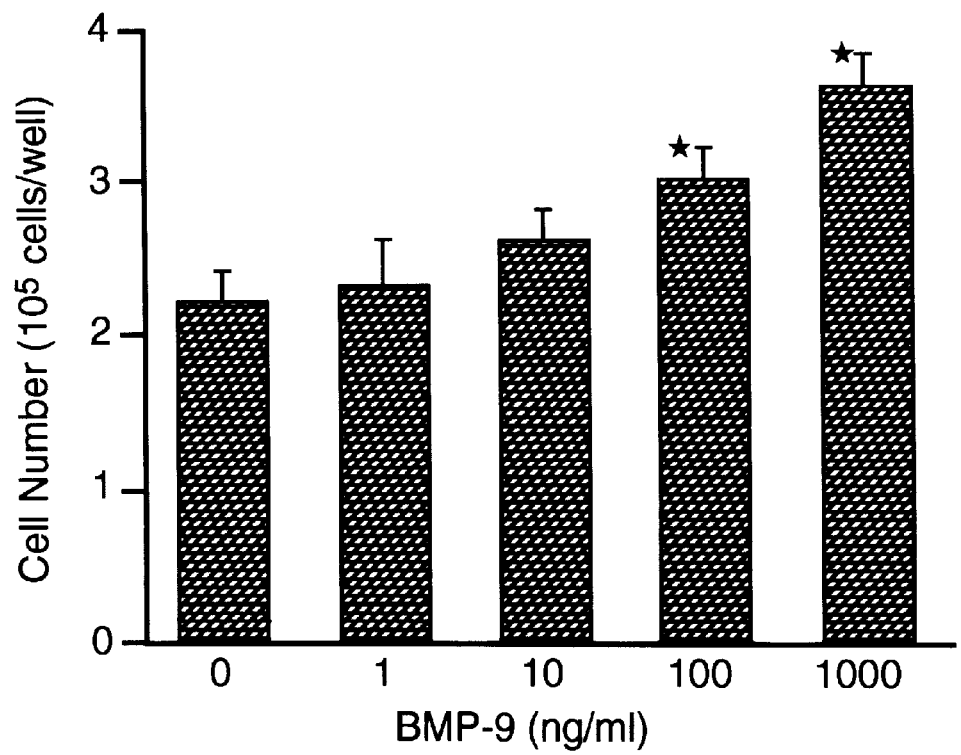

Fig. 6
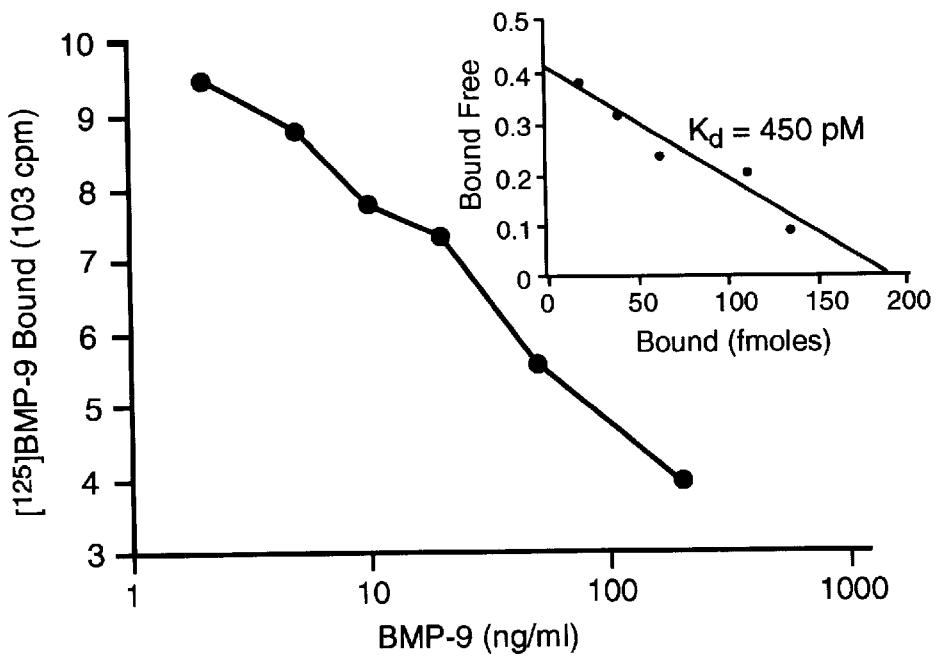
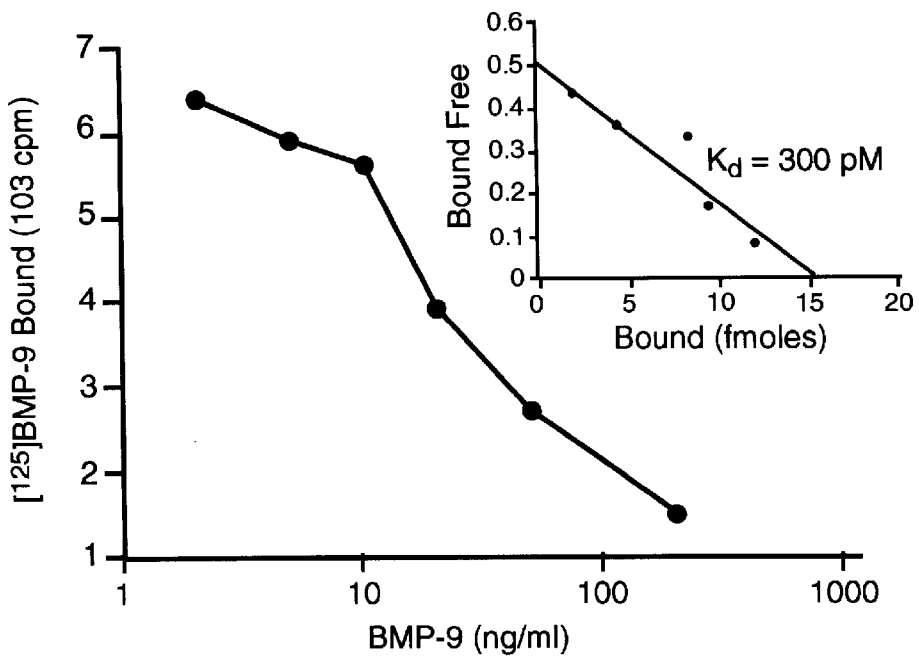

Fig. 8
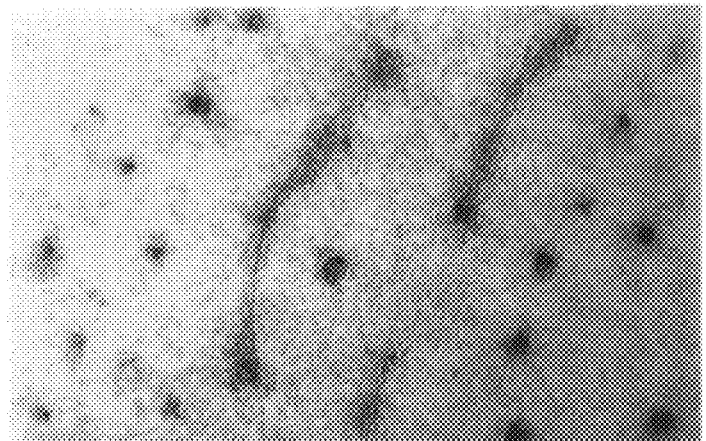
IMCD-3  Control  Day 6
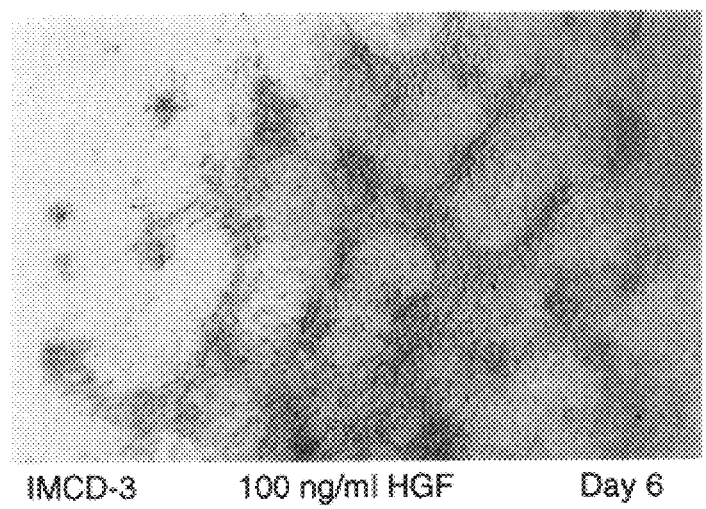
IMCD-3  100 ng/ml HGF  Day 6
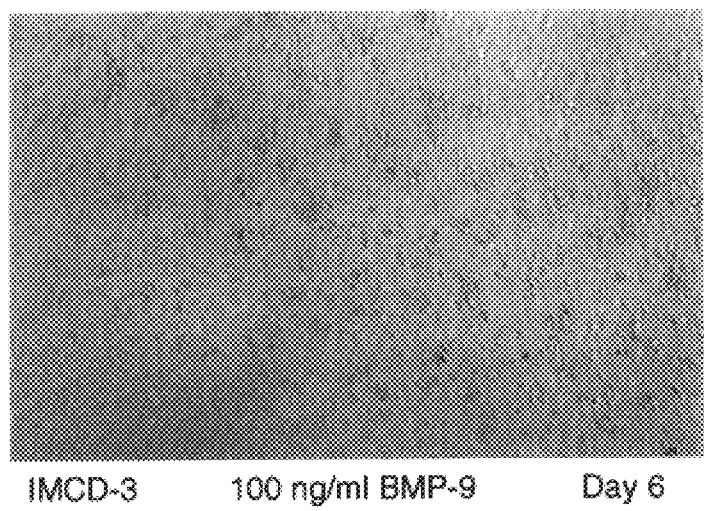
IMCD-3  100 ng/ml BMP-9  Day 6

PCR Analysis of BMP-9 mRNA in adult mouse tissues

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 2447 base pairs
      (B) TYPE: nucleic acid
      (C) STRANDEDNESS: double
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: Mus musculus
      (B) STRAIN: C57B46xCBA
      (F) TISSUE TYPE: liver (vii) IMMEDIATE SOURCE:
      (A) LIBRARY: Mouse liver cDNA
      (B) CLONE: ML14A (viii) POSITION IN GENOME:
      (C) UNITS: bp (ix) FEATURE:
      (A) NAME/KEY: mat_peptide
      (B) LOCATION: 1564..1893

-continued (ix) FEATURE:
    (A) NAME/KEY: CDS
    (B) LOCATION: 610..1896

(ix) FEATURE:
    (A) NAME/KEY: mRNA
    (B) LOCATION: 1..2447

(xi) SEQUENCE DESCRIPTION: SEQ ID NO:1:

```
CATTAATAAA TATTAAGTAT TGGAATTAGT GAAATTGGAG TTCCTTGTGG AAGGAAGTGG        60

GCAAGTGAGC TTTTTAGTTT GTGTCGGAAG CCTGTAATTA CGGCTCCAGC TCATAGTGGA       120

ATGGCTATAC TTAGATTTAT GGATAGTTGG GTAGTAGGTG TAAATGTATG TGGTAAAAGG       180

CCTAGGAGAT TTGTTGATCC AATAAATATG ATTAGGGAAA CAATTATTAG GGTTCATGTT       240

CGTCCTTTTG GTGTGTGGAT TAGCATTATT TGTTTGATAA TAAGTTTAAC TAGTCAGTGT       300

TGGAAAGAAT GGAGACGGTT GTTGATTAGG CGTTTTGAGG ATGGGAATAG GATTGAAGGA       360

AATATAATGA TGGCTACAAC GATTGGGAAT CCTATTATTG TTGGGGTAAT GAATGAGGCA       420

AATAGATTTT CGTTCATTTT AATTCTCAAG GGGTTTTTAC TTTTATGTTT GTTAGTGATA       480

TTGGTGAGTA GGCCAAGGGT TAATAGTGTA ATTGAATTAT AGTGAAATCA TATTACTAGA       540

CCTGATGTTA GAAGGAGGGC TGAAAAGGCT CCTTCCCTCC CAGGACAAAA CCGGAGCAGG       600

GCCACCCGG ATG TCC CCT GGG GCC TTC CGG GTG GCC CTG CTC CCG CTG          648
          Met Ser Pro Gly Ala Phe Arg Val Ala Leu Leu Pro Leu
              -318        -315            -310

TTC CTG CTG GTC TGT GTC ACA CAG CAG AAG CCG CTG CAG AAC TGG GAA         696
Phe Leu Leu Val Cys Val Thr Gln Gln Lys Pro Leu Gln Asn Trp Glu
-305             -300             -295             -290

CAA GCA TCC CCT GGG GAA AAT GCC CAC AGC TCC CTG GGA TTG TCT GGA         744
Gln Ala Ser Pro Gly Glu Asn Ala His Ser Ser Leu Gly Leu Ser Gly
             -285             -280             -275

GCT GGA GAG GAG GGT GTC TTT GAC CTG CAG ATG TTC CTG GAG AAC ATG         792
Ala Gly Glu Glu Gly Val Phe Asp Leu Gln Met Phe Leu Glu Asn Met
         -270             -265             -260

AAG GTG GAT TTC CTA CGC AGC CTT AAC CTC AGC GGC ATT CCC TCC CAG         840
Lys Val Asp Phe Leu Arg Ser Leu Asn Leu Ser Gly Ile Pro Ser Gln
    -255             -250             -245

GAC AAA ACC AGA GCG GAG CCA CCC CAG TAC ATG ATC GAC TTG TAC AAC         888
Asp Lys Thr Arg Ala Glu Pro Pro Gln Tyr Met Ile Asp Leu Tyr Asn
    -240             -235             -230

AGA TAC ACA ACG GAC AAA TCG TCT ACG CCT GCC TCC AAC ATC GTG CGG         936
Arg Tyr Thr Thr Asp Lys Ser Ser Thr Pro Ala Ser Asn Ile Val Arg
-225             -220             -215             -210

AGC TTC AGC GTG GAA GAT GCT ATA TCG ACA GCT GCC ACG GAG GAC TTC         984
Ser Phe Ser Val Glu Asp Ala Ile Ser Thr Ala Ala Thr Glu Asp Phe
    -205             -200             -195

CCC TTT CAG AAG CAC ATC CTG ATC TTC AAC ATC TCC ATC CCG AGG CAC        1032
Pro Phe Gln Lys His Ile Leu Ile Phe Asn Ile Ser Ile Pro Arg His
         -190             -185             -180

GAG CAG ATC ACC AGG GCT GAG CTC CGA CTC TAT GTC TCC TGC CAA AAT        1080
Glu Gln Ile Thr Arg Ala Glu Leu Arg Leu Tyr Val Ser Cys Gln Asn
         -175             -170             -165

GAT GTG GAC TCC ACT CAT GGG CTG GAA GGA AGC ATG GTC GTT TAT GAT        1128
Asp Val Asp Ser Thr His Gly Leu Glu Gly Ser Met Val Val Tyr Asp
     -160             -155             -150

GTT CTG GAG GAC AGT GAG ACT TGG GAC CAG GCC ACG GGG ACC AAG ACC        1176
Val Leu Glu Asp Ser Glu Thr Trp Asp Gln Ala Thr Gly Thr Lys Thr
-145             -140             -135             -130

TTC TTG GTA TCC CAG GAC ATT CGG GAC GAA GGA TGG GAG ACT TTA GAA        1224
```

```
        Phe Leu Val Ser Gln Asp Ile Arg Asp Glu Gly Trp Glu Thr Leu Glu
                    -125                -120                -115

GTA TCG AGT GCC GTG AAG CGG TGG GTC AGG GCA GAC TCC ACA ACA AAC         1272
Val Ser Ser Ala Val Lys Arg Trp Val Arg Ala Asp Ser Thr Thr Asn
            -110                -105                -100

AAA AAT AAG CTC GAG GTG ACA GTG CAG AGC CAC AGG GAG AGC TGT GAC         1320
Lys Asn Lys Leu Glu Val Thr Val Gln Ser His Arg Glu Ser Cys Asp
        -95                 -90                 -85

ACA CTG GAC ATC AGT GTC CCT CCA GGT TCC AAA AAC CTG CCC TTC TTT         1368
Thr Leu Asp Ile Ser Val Pro Pro Gly Ser Lys Asn Leu Pro Phe Phe
        -80                 -75                 -70

GTT GTC TTC TCC AAT GAC CGC AGC AAT GGG ACC AAG GAG ACC AGA CTG         1416
Val Val Phe Ser Asn Asp Arg Ser Asn Gly Thr Lys Glu Thr Arg Leu
-65                 -60                 -55                 -50

GAG CTG AAG GAG ATG ATC GGC CAT GAG CAG GAG ACC ATG CTT GTG AAG         1464
Glu Leu Lys Glu Met Ile Gly His Glu Gln Glu Thr Met Leu Val Lys
                -45                 -40                 -35

ACA GCC AAA AAT GCT TAC CAG GTG GCA GGT GAG AGC CAA GAG GAG GAG         1512
Thr Ala Lys Asn Ala Tyr Gln Val Ala Gly Glu Ser Gln Glu Glu Glu
            -30                 -25                 -20

GGT CTA GAT GGA TAC ACA GCT GTG GGA CCA CTT TTA GCT AGA AGG AAG         1560
Gly Leu Asp Gly Tyr Thr Ala Val Gly Pro Leu Leu Ala Arg Arg Lys
        -15                 -10                 -5

AGG AGC ACC GGA GCC AGC AGC CAC TGC CAG AAG ACT TCT CTC AGG GTG         1608
Arg Ser Thr Gly Ala Ser Ser His Cys Gln Lys Thr Ser Leu Arg Val
 1               5                  10                  15

AAC TTT GAG GAC ATC GGC TGG GAC AGC TGG ATC ATT GCA CCC AAG GAA         1656
Asn Phe Glu Asp Ile Gly Trp Asp Ser Trp Ile Ile Ala Pro Lys Glu
                 20                  25                  30

TAT GAC GCC TAT GAG TGT AAA GGG GGT TGC TTC TTC CCA TTG GCT GAT         1704
Tyr Asp Ala Tyr Glu Cys Lys Gly Gly Cys Phe Phe Pro Leu Ala Asp
             35                  40                  45

GAC GTG ACA CCC ACC AAA CAT GCC ATC GTG CAG ACC CTG GTG CAT CTC         1752
Asp Val Thr Pro Thr Lys His Ala Ile Val Gln Thr Leu Val His Leu
         50                  55                  60

GAG TTC CCC ACA AAG GTG GGC AAA GCC TGC TGC GTT CCC ACC AAA CTG         1800
Glu Phe Pro Thr Lys Val Gly Lys Ala Cys Cys Val Pro Thr Lys Leu
     65                  70                  75

AGT CCC ATC TCC ATC CTC TAC AAG GAT GAC ATG GGG GTG CCA ACC CTC         1848
Ser Pro Ile Ser Ile Leu Tyr Lys Asp Asp Met Gly Val Pro Thr Leu
 80                  85                  90                  95

AAG TAC CAC TAT GAG GGG ATG AGT GTG GCT GAG TGT GGG TGT AGG TAGTCCCT   1903
Lys Tyr His Tyr Glu Gly Met Ser Val Ala Glu Cys Gly Cys Arg
                 100                 105                 110

AGCCACCCAG GGTGGGGATA CAGGACATGG AAGAGGTTCT GGTACGGTCC TGCATCCTCC       1963

TGCGCATGGT ATGCCTAAGT TGATCAGAAA CCATCCTTGA GAAGAAAAGG AGTTAGTTGC       2023

CCTTCTTGTG TCTGGTGGGT CCCTCTGCTG AAGTGACAAT GACTGGGGTA TGCGGGCCTG       2083

TGGGCAGAGC AGGAGACCCT GGAAGGGTTA GTGGGTAGAA AGATGTCAAA AGGAAGCTG        2143

TGGGTAGATG ACCTGCACTC CAGTGATTAG AAGTCCAGCC TTACCTGTGA GAGAGCTCCT      2203

GGCATCTAAG AGAACTCTGC TTCCTCATCA TCCCCACCGA CTTGTTCTTC CTTGGGAGTG      2263

TGTCCTCAGG GAGAACAGCA TTGCTGTTCC TGTGCCTCAA GCTCCCAGCT GACTCTCCTG      2323

TGGCTCATAG GACTGAATGG GGTGAGGAAG AGCCTGATGC CCTCTGGCAA TCAGAGCCCG      2383

AAGGACTTCA AACATCTGG ACAACTCTCA TTGACTGATG CTCCAACATA ATTTTTAAAA       2443

AGAG                                                                   2447
```

(2) INFORMATION FOR SEQ ID NO:2:

(i) SEQUENCE CHARACTERISTICS:
        (A) LENGTH: 428 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Pro Gly Ala Phe Arg Val Ala Leu Leu Pro Leu Phe Leu Leu
-318            -315                -310                -305

Val Cys Val Thr Gln Gln Lys Pro Leu Gln Asn Trp Glu Gln Ala Ser
        -300                -295                -290

Pro Gly Glu Asn Ala His Ser Ser Leu Gly Leu Ser Gly Ala Gly Glu
    -285                -280                -275

Glu Gly Val Phe Asp Leu Gln Met Phe Leu Glu Asn Met Lys Val Asp
-270            -265                -260                -255

Phe Leu Arg Ser Leu Asn Leu Ser Gly Ile Pro Ser Gln Asp Lys Thr
                -250                -245                -240

Arg Ala Glu Pro Pro Gln Tyr Met Ile Asp Leu Tyr Asn Arg Tyr Thr
            -235                -230                -225

Thr Asp Lys Ser Ser Thr Pro Ala Ser Asn Ile Val Arg Ser Phe Ser
        -220                -215                -210

Val Glu Asp Ala Ile Ser Thr Ala Ala Thr Glu Asp Phe Pro Phe Gln
    -205                -200                -195

Lys His Ile Leu Ile Phe Asn Ile Ser Ile Pro Arg His Glu Gln Ile
-190            -185                -180                -175

Thr Arg Ala Glu Leu Arg Leu Tyr Val Ser Cys Gln Asn Asp Val Asp
            -170                -165                -160

Ser Thr His Gly Leu Glu Gly Ser Met Val Val Tyr Asp Val Leu Glu
        -155                -150                -145

Asp Ser Glu Thr Trp Asp Gln Ala Thr Gly Thr Lys Thr Phe Leu Val
    -140                -135                -130

Ser Gln Asp Ile Arg Asp Glu Gly Trp Glu Thr Leu Glu Val Ser Ser
    -125                -120                -115

Ala Val Lys Arg Trp Val Arg Ala Asp Ser Thr Thr Asn Lys Asn Lys
-110            -105                -100                -95

Leu Glu Val Thr Val Gln Ser His Arg Glu Ser Cys Asp Thr Leu Asp
            -90                 -85                 -80

Ile Ser Val Pro Pro Gly Ser Lys Asn Leu Pro Phe Phe Val Val Phe
        -75                 -70                 -65

Ser Asn Asp Arg Ser Asn Gly Thr Lys Glu Thr Arg Leu Glu Leu Lys
    -60                 -55                 -50

Glu Met Ile Gly His Glu Gln Glu Thr Met Leu Val Lys Thr Ala Lys
    -45                 -40                 -35

Asn Ala Tyr Gln Val Ala Gly Glu Ser Gln Glu Glu Gly Leu Asp
-30                 -25                 -20                 -15

Gly Tyr Thr Ala Val Gly Pro Leu Leu Ala Arg Arg Lys Arg Ser Thr
            -10                 -5                   1

Gly Ala Ser Ser His Cys Gln Lys Thr Ser Leu Arg Val Asn Phe Glu
            5                   10                  15

Asp Ile Gly Trp Asp Ser Trp Ile Ile Ala Pro Lys Glu Tyr Asp Ala
    20                  25                  30

Tyr Glu Cys Lys Gly Gly Cys Phe Phe Pro Leu Ala Asp Asp Val Thr
```

```
                35                    40                    45                    50
Pro Thr Lys His Ala Ile Val Gln Thr Leu Val His Leu Glu Phe Pro
                    55                    60                    65

Thr Lys Val Gly Lys Ala Cys Cys Val Pro Thr Lys Leu Ser Pro Ile
        70                    75                    80

Ser Ile Leu Tyr Lys Asp Asp Met Gly Val Pro Thr Leu Lys Tyr His
        85                    90                    95

Tyr Glu Gly Met Ser Val Ala Glu Cys Gly Cys Arg
100                   105                   110
```

(2) INFORMATION FOR SEQ ID NO:3:

(i) SEQUENCE CHARACTERISTICS:
        (A) LENGTH: 1954 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens
        (G) CELL TYPE: Osteosarcoma Cell Line
        (H) CELL LINE: U-20S (vii) IMMEDIATE SOURCE:
        (A) LIBRARY: U20S cDNA in Lambda gt10
        (B) CLONE: Lambda U20S-3

(viii) POSITION IN GENOME:
        (C) UNITS: bp (ix) FEATURE:
        (A) NAME/KEY: CDS
        (B) LOCATION: 403..1629

(ix) FEATURE:
        (A) NAME/KEY: mat_peptide
        (B) LOCATION: 1279..1626

(ix) FEATURE:
        (A) NAME/KEY: mRNA
        (B) LOCATION: 9..1934

(xi) SEQUENCE DESCRIPTION: SEQ ID NO:3:

```
CTCTAGAGGG CAGAGGAGGA GGGAGGGAGG GAAGGAGCGC GGAGCCCGGC CCGGAAGCTA      60

GGTGAGTGTG GCATCCGAGC TGAGGGACGC GAGCCTGAGA CGCCGCTGCT GCTCCGGCTG     120

AGTATCTAGC TTGTCTCCCC GATGGGATTC CCGTCCAAGC TATCTCGAGC CTGCAGCGCC     180

ACAGTCCCCG GCCCTCGCCC AGGTTCACTG CAACCGTTCA GAGGTCCCCA GGAGCTGCTG     240

CTGGCGAGCC CGCTACTGCA GGGACCTATG GAGCCATTCC GTAGTGCCAT CCCGAGCAAC     300

GCACTGCTGC AGCTTCCCTG AGCCTTTCCA GCAAGTTTGT TCAAGATTGG CTGTCAAGAA     360

TCATGGACTG TTATTATATG CCTTGTTTTC TGTCAAGACA CC ATG ATT CCT GGT       414
                                              Met Ile Pro Gly
                                              -292     -290

AAC CGA ATG CTG ATG GTC GTT TTA TTA TGC CAA GTC CTG CTA GGA GGC       462
Asn Arg Met Leu Met Val Val Leu Leu Cys Gln Val Leu Leu Gly Gly
        -285                    -280                    -275

GCG AGC CAT GCT AGT TTG ATA CCT GAG ACG GGG AAG AAA AAA GTC GCC       510
Ala Ser His Ala Ser Leu Ile Pro Glu Thr Gly Lys Lys Lys Val Ala
        -270                    -265                    -260
```

```
GAG ATT CAG GGC CAC GCG GGA GGA CGC CGC TCA GGG CAG AGC CAT GAG       558
Glu Ile Gln Gly His Ala Gly Gly Arg Arg Ser Gly Gln Ser His Glu
    -255                -250                -245

CTC CTG CGG GAC TTC GAG GCG ACA CTT CTG CAG ATG TTT GGG CTG CGC       606
Leu Leu Arg Asp Phe Glu Ala Thr Leu Leu Gln Met Phe Gly Leu Arg
-240                -235                -230                -225

CGC CGC CCG CAG CCT AGC AAG AGT GCC GTC ATT CCG GAC TAC ATG CGG       654
Arg Arg Pro Gln Pro Ser Lys Ser Ala Val Ile Pro Asp Tyr Met Arg
                -220                -215                -210

GAT CTT TAC CGG CTT CAG TCT GGG GAG GAG GAG GAA GAG CAG ATC CAC       702
Asp Leu Tyr Arg Leu Gln Ser Gly Glu Glu Glu Glu Glu Gln Ile His
            -205                -200                -195

AGC ACT GGT CTT GAG TAT CCT GAG CGC CCG GCC AGC CGG GCC AAC ACC       750
Ser Thr Gly Leu Glu Tyr Pro Glu Arg Pro Ala Ser Arg Ala Asn Thr
        -190                -185                -180

GTG AGG AGC TTC CAC CAC GAA GAA CAT CTG GAG AAC ATC CCA GGG ACC       798
Val Arg Ser Phe His His Glu Glu His Leu Glu Asn Ile Pro Gly Thr
    -175                -170                -165

AGT GAA AAC TCT GCT TTT CGT TTC CTC TTT AAC CTC AGC AGC ATC CCT       846
Ser Glu Asn Ser Ala Phe Arg Phe Leu Phe Asn Leu Ser Ser Ile Pro
-160                -155                -150                -145

GAG AAC GAG GTG ATC TCC TCT GCA GAG CTT CGG CTC TTC CGG GAG CAG       894
Glu Asn Glu Val Ile Ser Ser Ala Glu Leu Arg Leu Phe Arg Glu Gln
                -140                -135                -130

GTG GAC CAG GGC CCT GAT TGG GAA AGG GGC TTC CAC CGT ATA AAC ATT       942
Val Asp Gln Gly Pro Asp Trp Glu Arg Gly Phe His Arg Ile Asn Ile
            -125                -120                -115

TAT GAG GTT ATG AAG CCC CCA GCA GAA GTG GTG CCT GGG CAC CTC ATC       990
Tyr Glu Val Met Lys Pro Pro Ala Glu Val Val Pro Gly His Leu Ile
        -110                -105                -100

ACA CGA CTA CTG GAC ACG AGA CTG GTC CAC CAC AAT GTG ACA CGG TGG      1038
Thr Arg Leu Leu Asp Thr Arg Leu Val His His Asn Val Thr Arg Trp
    -95                 -90                 -85

GAA ACT TTT GAT GTG AGC CCT GCG GTC CTT CGC TGG ACC CGG GAG AAG      1086
Glu Thr Phe Asp Val Ser Pro Ala Val Leu Arg Trp Thr Arg Glu Lys
-80                 -75                 -70                 -65

CAG CCA AAC TAT GGG CTA GCC ATT GAG GTG ACT CAC CTC CAT CAG ACT      1134
Gln Pro Asn Tyr Gly Leu Ala Ile Glu Val Thr His Leu His Gln Thr
                -60                 -55                 -50

CGG ACC CAC CAG GGC CAG CAT GTC AGG ATT AGC CGA TCG TTA CCT CAA      1182
Arg Thr His Gln Gly Gln His Val Arg Ile Ser Arg Ser Leu Pro Gln
            -45                 -40                 -35

GGG AGT GGG AAT TGG GCC CAG CTC CGG CCC CTC CTG GTC ACC TTT GGC      1230
Gly Ser Gly Asn Trp Ala Gln Leu Arg Pro Leu Leu Val Thr Phe Gly
        -30                 -25                 -20

CAT GAT GGC CGG GGC CAT GCC TTG ACC CGA CGC CGG AGG GCC AAG CGT      1278
His Asp Gly Arg Gly His Ala Leu Thr Arg Arg Arg Arg Ala Lys Arg
    -15                 -10                 -5

AGC CCT AAG CAT CAC TCA CAG CGG GCC AGG AAG AAG AAT AAG AAC TGC      1326
Ser Pro Lys His His Ser Gln Arg Ala Arg Lys Lys Asn Lys Asn Cys
 1                   5                  10                  15

CGG CGC CAC TCG CTC TAT GTG GAC TTC AGC GAT GTG GGC TGG AAT GAC      1374
Arg Arg His Ser Leu Tyr Val Asp Phe Ser Asp Val Gly Trp Asn Asp
                 20                  25                  30

TGG ATT GTG GCC CCA CCA GGC TAC CAG GCC TTC TAC TGC CAT GGG GAC      1422
Trp Ile Val Ala Pro Pro Gly Tyr Gln Ala Phe Tyr Cys His Gly Asp
             35                  40                  45

TGC CCC TTT CCA CTG GCT GAC CAC CTC AAC TCA ACC AAC CAT GCC ATT      1470
Cys Pro Phe Pro Leu Ala Asp His Leu Asn Ser Thr Asn His Ala Ile
 50                  55                  60
```

```
GTG CAG ACC CTG GTC AAT TCT GTC AAT TCC AGT ATC CCC AAA GCC TGT    1518
Val Gln Thr Leu Val Asn Ser Val Asn Ser Ser Ile Pro Lys Ala Cys
 65                  70                  75                  80

TGT GTG CCC ACT GAA CTG AGT GCC ATC TCC ATG CTG TAC CTG GAT GAG    1566
Cys Val Pro Thr Glu Leu Ser Ala Ile Ser Met Leu Tyr Leu Asp Glu
                 85                  90                  95

TAT GAT AAG GTG GTA CTG AAA AAT TAT CAG GAG ATG GTA GTA GAG GGA    1614
Tyr Asp Lys Val Val Leu Lys Asn Tyr Gln Glu Met Val Val Glu Gly
            100                 105                 110

TGT GGG TGC CGC TGAGATCAGG CAGTCCTTGA GGATAGACAG ATATACACAC        1666
Cys Gly Cys Arg
            115

CACACACACA CACCCACATAC ACCACACACA CACGTTCCCA TCCACTCACC CACACACTAC  1726

ACAGACTGCT TCCTTATAGC TGGACTTTTA TTTAAAAAAA AAAAAAAAAA AATGGAAAAA  1786

ATCCCTAAAC ATTCACCTTG ACCTTATTTA TGACTTTACG TGCAAATGTT TTGACCATAT  1846

TGATCATATA TTTTGACAAA ATATATTTAT AACTACGTAT TAAAAGAAAA AAATAAAATG  1906

AGTCATTATT TTAAAAAAAA AAAAAAAACT CTAGAGTCGA CGGAATTC              1954

(2) INFORMATION FOR SEQ ID NO:4:

(i) SEQUENCE CHARACTERISTICS:
        (A) LENGTH: 408 amino acids
        (B) TYPE: amino acid
        (D) TOPOLOGY: linear (ii) MOLECULE TYPE: protein (xi) SEQUENCE DESCRIPTION: SEQ ID NO:4:

Met Ile Pro Gly Asn Arg Met Leu Met Val Val Leu Leu Cys Gln Val
-292     -290                -285                -280

Leu Leu Gly Gly Ala Ser His Ala Ser Leu Ile Pro Glu Thr Gly Lys
        -275                -270                -265

Lys Lys Val Ala Glu Ile Gln Gly His Ala Gly Gly Arg Arg Ser Gly
-260                -255                -250                -245

Gln Ser His Glu Leu Leu Arg Asp Phe Glu Ala Thr Leu Leu Gln Met
            -240                -235                -230

Phe Gly Leu Arg Arg Arg Pro Gln Pro Ser Lys Ser Ala Val Ile Pro
        -225                -220                -215

Asp Tyr Met Arg Asp Leu Tyr Arg Leu Gln Ser Gly Glu Glu Glu Glu
            -210                -205                -200

Glu Gln Ile His Ser Thr Gly Leu Glu Tyr Pro Glu Arg Pro Ala Ser
        -195                -190                -185

Arg Ala Asn Thr Val Arg Ser Phe His His Glu Glu His Leu Glu Asn
-180                -175                -170                -165

Ile Pro Gly Thr Ser Glu Asn Ser Ala Phe Arg Phe Leu Phe Asn Leu
            -160                -155                -150

Ser Ser Ile Pro Glu Asn Glu Val Ile Ser Ser Ala Glu Leu Arg Leu
        -145                -140                -135

Phe Arg Glu Gln Val Asp Gln Gly Pro Asp Trp Glu Arg Gly Phe His
    -130                -125                -120

Arg Ile Asn Ile Tyr Glu Val Met Lys Pro Pro Ala Glu Val Val Pro
    -115                -110                -105

Gly His Leu Ile Thr Arg Leu Leu Asp Thr Arg Leu Val His His Asn
-100                 -95                 -90                 -85

Val Thr Arg Trp Glu Thr Phe Asp Val Ser Pro Ala Val Leu Arg Trp
```

```
                -80              -75              -70
Thr Arg Glu Lys Gln Pro Asn Tyr Gly Leu Ala Ile Glu Val Thr His
            -65              -60              -55

Leu His Gln Thr Arg Thr His Gln Gly Gln His Val Arg Ile Ser Arg
    -50              -45              -40

Ser Leu Pro Gln Gly Ser Gly Asn Trp Ala Gln Leu Arg Pro Leu Leu
    -35              -30              -25

Val Thr Phe Gly His Asp Gly Arg Gly His Ala Leu Thr Arg Arg Arg
-20              -15              -10                           -5

Arg Ala Lys Arg Ser Pro Lys His His Ser Gln Arg Ala Arg Lys Lys
                1                5                   10

Asn Lys Asn Cys Arg Arg His Ser Leu Tyr Val Asp Phe Ser Asp Val
            15              20              25

Gly Trp Asn Asp Trp Ile Val Ala Pro Pro Gly Tyr Gln Ala Phe Tyr
    30              35              40

Cys His Gly Asp Cys Pro Phe Pro Leu Ala Asp His Leu Asn Ser Thr
    45              50              55                       60

Asn His Ala Ile Val Gln Thr Leu Val Asn Ser Val Asn Ser Ser Ile
            65              70              75

Pro Lys Ala Cys Cys Val Pro Thr Glu Leu Ser Ala Ile Ser Met Leu
            80              85              90

Tyr Leu Asp Glu Tyr Asp Lys Val Val Leu Lys Asn Tyr Gln Glu Met
    95              100             105

Val Val Glu Gly Cys Gly Cys Arg
    110             115
```

(2) INFORMATION FOR SEQ ID NO:5:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:5:

CATGGGCAGC TCGAG                                                          15

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:6:

CTGCAGGCGA GCCTGAATTC CTCGAGCCAT CATG                                     34

(2) INFORMATION FOR SEQ ID NO:7:

(i) SEQUENCE CHARACTERISTICS:
        (A) LENGTH: 68 base pairs
        (B) TYPE: nucleic acid
        (C) STRANDEDNESS: double
        (D) TOPOLOGY: linear (ii) MOLECULE TYPE: cDNA to mRNA -continued (xi) SEQUENCE DESCRIPTION: SEQ ID NO:7:

```
CGAGGTTAAA AAACGTCTAG GCCCCCCGAA CCACGGGGAC GTGGTTTTCC TTTGAAAAAC      60

ACGATTGC                                                              68
```

(2) INFORMATION FOR SEQ ID NO:8:

(i) SEQUENCE CHARACTERISTICS:
        (A) LENGTH: 470 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (v) FRAGMENT TYPE: C-terminal (vi) ORIGINAL SOURCE:
        (A) ORGANISM: Homo sapiens
        (H) CELL LINE: W138 (genomic DNA)

(vii) IMMEDIATE SOURCE:
        (A) LIBRARY: human genomic library
        (B) CLONE: lambda 111-1

(viii) POSITION IN GENOME:
        (C) UNITS: bp (ix) FEATURE:
        (A) NAME/KEY: exon
        (B) LOCATION: 1..470

(ix) FEATURE:
        (A) NAME/KEY: CDS
        (B) LOCATION: 1..456

(ix) FEATURE:
        (A) NAME/KEY: mat_peptide
        (B) LOCATION: 124..453

(ix) FEATURE:
        (A) NAME/KEY: mRNA
        (B) LOCATION: 1..470

(xi) SEQUENCE DESCRIPTION: SEQ ID NO:8:

```
TGA ACA AGA GAG TGC TCA AGA AGC TGT CCA AGG ACG GCT CCA CAG AGG       48
Thr Arg Glu Cys Ser Arg Ser Cys Pro Arg Thr Ala Pro Gln Arg
    -40             -35                 -30

CAG GTG AGA GCA GTC ACG AGG AGG ACA CGG ATG GCG CAC GTG GCT GCG       96
Gln Val Arg Ala Val Thr Arg Arg Thr Arg Met Ala His Val Ala Ala
-25             -20                 -15                 -10

GGG TCG ACT TTA GCC AGG CGG AAA AGG AGC GCC GGG GCT GGC AGC CAC      144
Gly Ser Thr Leu Ala Arg Arg Lys Arg Ser Ala Gly Ala Gly Ser His
            -5                   1                   5

TGT CAA AAG ACC TCC CTG CGG GTA AAC TTC GAG GAC ATC GGC TGG GAC      192
Cys Gln Lys Thr Ser Leu Arg Val Asn Phe Glu Asp Ile Gly Trp Asp
        10                  15                  20

AGC TGG ATC ATT GCA CCC AAG GAG TAT GAA GCC TAC GAG TGT AAG GGC      240
Ser Trp Ile Ile Ala Pro Lys Glu Tyr Glu Ala Tyr Glu Cys Lys Gly
    25                  30                  35

GGC TGC TTC TTC CCC TTG GCT GAC GAT GTG ACG CCG ACG AAA CAC GCT      288
Gly Cys Phe Phe Pro Leu Ala Asp Asp Val Thr Pro Thr Lys His Ala
40                  45                  50                  55

ATC GTG CAG ACC CTG GTG CAT CTC AAG TTC CCC ACA AAG GTG GGC AAG      336
Ile Val Gln Thr Leu Val His Leu Lys Phe Pro Thr Lys Val Gly Lys
            60                  65                  70

GCC TGC TGT GTG CCC ACC AAA CTG AGC CCC ATC TCC GTC CTC TAC AAG      384
```

```
Ala Cys Cys Val Pro Thr Lys Leu Ser Pro Ile Ser Val Leu Tyr Lys
            75                  80                  85

GAT GAC ATG GGG GTG CCC ACC CTC AAG TAC CAT TAC GAG GGC ATG AGC      432
Asp Asp Met Gly Val Pro Thr Leu Lys Tyr His Tyr Glu Gly Met Ser
        90                  95                 100

GTG GCA GAG TGT GGG TGC AGG TAGTATCTGC CTGCGGG                        470
Val Ala Glu Cys Gly Cys Arg
    105                 110
```

(2) INFORMATION FOR SEQ ID NO:9:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:9:

```
Thr Arg Glu Cys Ser Arg Ser Cys Pro Arg Thr Ala Pro Gln Arg
-40                 -35                 -30

Gln Val Arg Ala Val Thr Arg Arg Thr Arg Met Ala His Val Ala Ala
-25                 -20                 -15                 -10

Gly Ser Thr Leu Ala Arg Arg Lys Arg Ser Ala Gly Ala Gly Ser His
                -5                   1                   5

Cys Gln Lys Thr Ser Leu Arg Val Asn Phe Glu Asp Ile Gly Trp Asp
        10                  15                  20

Ser Trp Ile Ile Ala Pro Lys Glu Tyr Glu Ala Tyr Glu Cys Lys Gly
    25                  30                  35

Gly Cys Phe Phe Pro Leu Ala Asp Asp Val Thr Pro Thr Lys His Ala
40                  45                  50                  55

Ile Val Gln Thr Leu Val His Leu Lys Phe Pro Thr Lys Val Gly Lys
            60                  65                  70

Ala Cys Cys Val Pro Thr Lys Leu Ser Pro Ile Ser Val Leu Tyr Lys
            75                  80                  85

Asp Asp Met Gly Val Pro Thr Leu Lys Tyr His Tyr Glu Gly Met Ser
        90                  95                 100

Val Ala Glu Cys Gly Cys Arg
    105                 110
```

(2) INFORMATION FOR SEQ ID NO:10:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:10:

```
CTATGAGTGT AAAGGGGGTT GCTTCTTCCC ATTGGCTGAT                            40
```

(2) INFORMATION FOR SEQ ID NO:11:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:11:

GTGCCAACCC TCAAGTACCA CTATGAGGGG ATGAGTGTGG                              40

(2) INFORMATION FOR SEQ ID NO:12:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:12:

ATCGGGCCCC TTTTAGCCAG GCGGAAAAGG AG                                      32

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:13:

AGCGAATTCC CCGCAGGCAG ATACTACCTG                                         30

(2) INFORMATION FOR SEQ ID NO:14:

(i) SEQUENCE CHARACTERISTICS:
        (A) LENGTH: 61 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:14:

GATTCCGTCG ACCACCATGT CCCCTGGGGC CTGGTCTAGA TGGATACACA GCTGTGGGGC        60

C                                                                        61

(2) INFORMATION FOR SEQ ID NO:15:

(i) SEQUENCE CHARACTERISTICS:
        (A) LENGTH: 52 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:15:

CCACAGCTGT GTATCCATCT AGACCAGGCC CCAGGGGACA TGGTGGTCGA CG                52

(2) INFORMATION FOR SEQ ID NO:16:

(i) SEQUENCE CHARACTERISTICS:
        (A) LENGTH: 113 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:16:

-continued

```
GATTCCGTCG ACCACCATGT CCCCTGGGGC CTGGTCTAGA TGGATACACA GCTGTGGGGC         60

CGCAGCTGGT GGTACAGGGG ACCCCGGACC AGATCTACCT ATGTGTCGAC ACC              113

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:17:

TCGACCACCA TGTCCCCTGG                                                    20

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:18:

GCCCCAGGGG ACATGGTGG                                                     19

(2) INFORMATION FOR SEQ ID NO:19:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:19:

TCGACCACCA TGTCCCCTGG GGTGGTACAG GGGACCCCG                               39
```

BONE MORPHOGENETIC PROTEIN (BMP)-9 COMPOSITIONS AND THEIR USES

The present invention relates to a novel family of purified proteins designated BMP-9 proteins and processes for obtaining them. These proteins may be used to induce bone and/or cartilage formation or other connective tissue formation, in wound healing and tissue repair, in hepatic growth and function, and in regulating lung and kidney cell function.

The murine BMP-9 DNA sequence is set forth in SEQ ID NO:1 and amino acid sequence in SEQ ID NO:2. Human BMP-9 sequence is set forth in SEQ ID NO:8 and SEQ ID NO:9. It is contemplated that BMP-9 proteins are capable of inducing the formation of cartilage and/or bone. BMP-9 proteins may be further characterized by the ability to demonstrate cartilage and/or bone formation activity in the rat bone formation assay described below. The proteins or compositions of the present invention may be further characterized by the ability to demonstrate effects upon the growth and/or differentiation of embryonic cells and/or stem cells.

Murine BMP-9 is characterized by comprising amino acid #1–110 (SEQ ID NO:2). Murine BMP-9 may be produced by culturing a cell transformed with a DNA sequence comprising nucleotide #610 to nucleotide #1893 (SEQ ID NO:1) and recovering and purifying from the culture medium a protein characterized by the amino acid sequence comprising amino acid #1 to #110 (SEQ ID NO:2) substantially free from other proteinaceous materials with which it is co-produced.

Human BMP-9 is expected to be homologous to murine BMP-9 and is characterized by comprising amino acid #1 (Ser, Ala, Gly) to #110 (Arg) (SEQ ID NO:9). The invention includes methods for obtaining the DNA sequences encoding human BMP-9. This method entails utilizing the murine BMP-9 nucleotide sequence or portions thereof to design probes to screen libraries for the human gene or fragments thereof using standard techniques. Human BMP-9 may be produced by culturing a cell transformed with the BMP-9 DNA sequence and recovering and purifying BMP-9 from the culture medium. The expressed protein is isolated, recovered, and purified from the culture medium. The purified expressed protein is substantially free from other proteinaceous materials with which it is co-produced, as well as from other contaminants. The recovered purified protein is contemplated to exhibit cartilage and/or bone formation activity. The proteins of the invention may be further characterized by the ability to demonstrate cartilage and/or bone formation activity in the rat bone formation assay described below.

Human BMP-9 may be produced by culturing a cell transformed with a DNA sequence comprising nucleotide #124 to #453 as shown in SEQ ID NO:8 and recovering and purifying from the culture medium a protein characterized by the amino acid sequence of SEQ ID NO:9 from amino acid #1 to amino acid #110 substantially free from other proteinaceous materials with which it is co-produced.

Another aspect of the invention provides pharmaceutical compositions containing a therapeutically effective amount of a BMP-9 protein in a pharmaceutically acceptable vehicle or carrier. BMP-9 compositions of the invention may be used in the formation of cartilage. These compositions may further be utilized for the formation of bone. BMP-9 compositions may also be used for wound healing and tissue repair. Compositions of the invention may further include at least one other therapeutically useful agent such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035, or BMP-15, disclosed in co-pending patent application, U.S. Pat. No. 5,635,372, filed on May 18, 1995.

The compositions of the invention may comprise, in addition to a BMP-9 protein, other therapeutically useful agents including growth factors such as epidermal growth factor (EGF), fibroblast growth factor (FGF), transforming growth factor (TGF-α and TGF-β), activins, inhibins and insulin-like growth factor (IGF). The compositions may also include an appropriate matrix for instance, for supporting the composition and providing a surface for bone and/or cartilage growth. The matrix may provide slow release of the osteoinductive protein and/or the appropriate environment for presentation thereof.

The BMP-9 compositions may be employed in methods for treating a number of bone and/or cartilage and/or other connective tissue defects, periodontal disease and various types of wounds. The tissue which may be treated include epidermis, nerve, muscle, including cardiac muscle, and other tissues and wounds, and other organs such as liver, lung, cardiac, pancreas and kidney tissue. These methods, according to the invention, entail administering to a patient needing such bone and/or cartilage formation wound healing or tissue repair, an effective amount of a BMP-9 protein. The BMP-9 containing compositions may also be used to treat or prevent other abnormalities of bone, cartilage, muscle, tendon, ligament or other connective tissue, organs such as liver, lung, cardiac, pancreas and kidney tissue, and other tissues. These methods may also entail the administration of a protein of the invention in conjunction with at least one of the novel BMP proteins disclosed in the co-owned applications described above. In addition, these methods may also include the administration of a BMP-9 protein with other growth factors including EGF, FGF, TGF-α, TGF-β, and IGF.

Still a further aspect of the invention are DNA sequences coding for expression of a BMP-9 protein. Such sequences include the sequence of nucleotides in a 5' to 3' direction illustrated in SEQ ID NO:1 and SEQ ID NO:8 or DNA sequences which hybridize under stringent conditions with the DNA sequences of SEQ ID NO:1 or SEQ ID NO:8 and encode a protein having the ability to induce the formation of cartilage and/or bone and/or other connective tissue, or other organs such as liver, lung, cardiac, pancreas and kidney tissue. Preferred DNA sequences include those which hybridize under stringent conditions (see, T. Maniatis et al. *Molecular Cloning A Laboratory Manual*), Cold Spring Harbor Laboratory (1982), pages 387 to 389). It is generally preferred that such DNA sequences encode a polypeptide which is at least 80% homologous, and more preferably at least about 90% homologous, to the mature human BMP-9 amino acid sequence shown in SEQ ID NO:9. Finally, allelic or other variations of the sequences of SEQ ID NO:1 or SEQ ID NO:8, whether such nucleotide changes result in changes in the peptide sequence or not, but where the peptide sequence still has BMP-9 activity are also included in the present invention. The present invention also includes fragments of the DNA sequence of BMP-9 shown in SEQ ID NO:8 which encode a polypeptide which retains the activity of BMP-9 protein.

The DNA sequences of the present invention are useful, for example, as probes for the detection of mRNA encoding BMP-9 in a given cell population. Thus, the present invention includes methods of detecting or diagnosing genetic disorders involving the BMP-9 gene, or disorders involving cellular, organ or tissue disorders in which BMP-9 is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a BMP-9 protein of the invention in which a cell line transformed with a DNA sequence encoding a BMP-9 protein in operative association with an expression control sequence therefor, is cultured in a suitable culture medium and a BMP-9 protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Other aspects and advantages of the present invention will be apparent upon consideration of the following detailed description and preferred embodiments thereof.

BRIEF DESCRIPTION OF THE DRAWINGS

FIG. 3 sets forth results of stimulation of HepG2 cell proliferation by BMP-9.

FIG. 6 sets forth results of rhBMP-9 binding to rat lung and kidney plasma membranes prepared from adult rat lung (upper panel) and kidney (lower panel). Data shown are representative of three experiments.

FIG. 8 sets forth inhibition of IMCD-3 cell condensation and tubulogenesis by rhBMP-9. Cells photographed after 6 days of treatment are representative of three experiments.

DETAILED DESCRIPTION OF THE INVENTION

Figure 1:
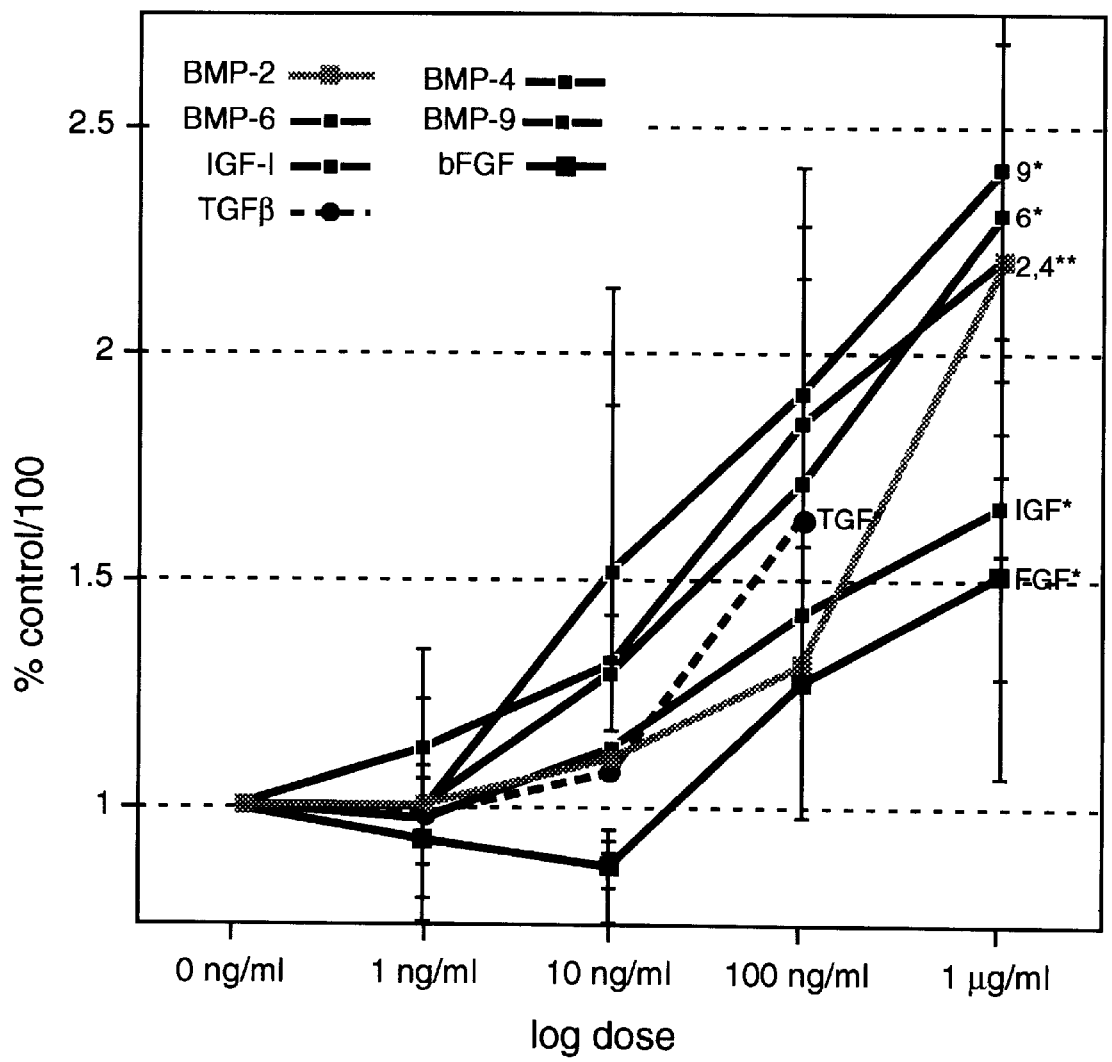
FIG. 1 sets forth articular cartilage assay sulfate incorporation results.

The murine BMP-9 nucleotide sequence is depicted in SEQ ID NO:1 and encoded amino acid sequence in SEQ ID NO:2. Purified murine BMP-9 proteins of the present invention are produced by culturing a host cell transformed with a DNA sequence comprising the DNA coding sequence of SEQ ID NO:1 from nucleotide #610 to nucleotide #1893 and recovering and purifying from the culture medium a protein which contains the amino acid sequence or a substantially homologous sequence as represented by amino acid #1 to #110 of SEQ ID NO:2. The BMP-9 proteins recovered from the culture medium are purified by isolating them from other proteinaceous materials from which they are co-produced and from other contaminants present.

Human BMP-9 nucleotide and amino acid sequence is depicted in SEQ ID NOS: 8 and 9. Mature human BMP-9 is expected to comprise amino acid #1 (Ser, Ala, Gly) to #110 (Arg).

Human BMP-9 may be produced by culturing a cell transformed with a DNA sequence comprising nucleotide #124 to #453 as shown in SEQ ID NO:8 and recovering and purifying from the culture medium a protein characterized by the amino acid sequence of SEQ ID NO:9 from amino acid #1 to amino acid #110 substantially free from other proteinaceous materials with which it is co-produced. For production in mammalian cells, the DNA sequence further comprises a DNA sequence encoding a suitable propeptide 5' to and lined in frame to the nucleotide sequence encoding the mature BMP-9-related polypeptide. The propeptide may be the native BMP-9-related propeptide, or may be a propeptide from another protein of the TGF-β superfamily. BMP-9 proteins may be characterized by the ability to induce the formation of cartilage. BMP-9 proteins may be further characterized by the ability to induce the formation of bone. BMP-9 proteins may be further characterized by the ability to demonstrate cartilage and/or bone formation activity in the rat bone formation assay described below. BMP-9 proteins may be further characterized by the ability to demonstrate effects upon the growth and/or differentiation of embryonic cells and/or stem cells. The proteins or compositions of the present invention may also be useful for treating cell populations, such as embryonic cells or stem cell populations, to enhance or enrich the growth and/or differentiation of the cells.

The BMP-9 proteins provided herein also include factors encoded by the sequences similar to those of SEQ ID NOS:1 and 8, but into which modifications are naturally provided (e.g., allelic variations in the nucleotide sequence which may result in amino acid changes in the polypeptide) or deliberately engineered, the protein retains the ability to induce the formation of cartilage and/or bone and/or other connective tissue, or other organs such as liver, lung, cardiac, pancreas and kidney tissue, or other activity characteristic of BMP-9. For example, synthetic polypeptides may wholly or partially duplicate continuous sequences of the amino acid residues of SEQ ID NOS:2 and 9. Preferred polypeptides include a polypeptide which is at least about 80% homologous, and more preferably at least about 90% homologous, to the mature human BMP-9 amino acid sequence shown in SEQ ID NO:9. Finally, allelic or other variations of the sequences of SEQ ID NO:9, whether such amino acid changes are induced by mutagenesis, chemical alteration, or by alteration of DNA sequence used to produce the polypeptide, where the peptide sequence still has BMP-9 activity, are also included in the present invention. The present invention also includes fragments of the amino acid sequence of BMP-9 shown in SEQ ID NO:9 which retain the activity of BMP-9 protein. These sequences, by virtue of sharing primary, secondary, or tertiary structural and conformational characteristics with BMP-9 polypeptides of SEQ ID NOS: 2 and 9 may possess biological properties in common therewith. Thus, they may be employed as biologically active substitutes for naturally-occurring BMP-9 and other BMP-9 polypeptides in therapeutic processes.

Other specific mutations of the sequences of BMP-9 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for BMP-9 proteins. These DNA sequences include those depicted in FIG. 1 or FIG. 3 (SEQ ID NOS:1 and 8) in a 5' to 3' direction and those sequences which hybridize thereto under stringent hybridization conditions [see, T. Maniatis et al., *Molecular Cloning* (*A Laboratory Manual*), Cold Spring Harbor Laboratory (1982), pages 387 to 389] and encode a protein having cartilage and/or bone and/or other connective tissue inducing activity or other organs such as liver, lung, cardiac, pancreas and kidney tissue.

Similarly, DNA sequences which code for BMP-9 proteins coded for by the sequences of SEQ ID NOS: 1 and 8, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NOS:1 and 8 which are caused by point mutations or by induced modifications (including insertion, deletion, and substitution) to enhance the activity, half-life or production of the polypeptides encoded are also encompassed in the invention.

Another aspect of the present invention provides a novel method for producing BMP-9 proteins. The method of the present invention involves culturing a suitable cell line, which has been transformed with a DNA sequence encoding a BMP-9 protein of the invention, under the control of known regulatory sequences. The transformed host cells are cultured and the BMP-9 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See e.g., Gething and Sambrook, Nature 293:620–625 (1981), or alternatively, Kaufman et al., Mol. Cell. Biol. 5(7):1750–1759 (1985) or Howley et al., U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See e.g., Miller et al., Genetic Engineering 8:277–298 (Plenum Press 1986) and references cited therein.

Another aspect of the present invention provides vectors for use in the method of expression of these novel BMP-9 polypeptides. Preferably the vectors contain the full novel DNA sequences described above which encode the novel factors of the invention. Additionally the vectors also contain appropriate expression control sequences permitting expression of the BMP-9 protein sequences. Alternatively, vectors incorporating modified sequences as described above are also embodiments of the present invention. Additionally, the sequence of SEQ ID NO:8 or other sequences encoding BMP-9 proteins could be manipulated to express a mature BMP-9 protein by deleting BMP-9 propeptide sequences and replacing them with sequences encoding the complete propeptides of other BMP proteins or members of the TGF-β superfamily. Thus, the present invention includes chimeric DNA molecules encoding a propeptide from a member of the TGF-β superfamily linked in correct reading frame to a DNA sequence encoding a BMP-9 polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

The purified proteins of the present invention may be used to generate antibodies, either monoclonal or polyclonal, to human BMP-9 and/or other BMP-9-related proteins, using methods that are known in the art of antibody production. Thus, the present invention also includes antibodies to human BMP-9 and/or other related proteins. The antibodies may be useful for purification of BMP-9 and/or other BMP-9-related proteins, or for inhibiting or preventing the effects of BMP-9-related proteins.

A protein of the present invention, which induces cartilage and/or bone formation in circumstances where bone is not normally formed, has application in the healing of bone fractures and cartilage defects in humans and other animals. Such a preparation employing a BMP-9 protein may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-9 protein may be used in the treatment of periodontal disease, and in other tooth repair processes. Such agents may provide an environment to attract bone-forming cells, stimulate growth of bone-forming cells or induce differentiation of progenitors of bone-forming cells, and may also support the regeneration of the periodontal ligament and attachment apparatus, which connects bone and teeth. BMP-9 polypeptides of the invention may also be useful in the treatment of osteoporosis. BMP-9 may be used in cartilage defect repair and prevention/reversal of osteoarthritis. A variety of osteogenic, cartilage-inducing and bone inducing factors have been described. See e.g., European Patent Application Nos. 148, 155 and 169,016 for discussions thereof.

The proteins of the invention may also be used in wound healing and related tissue repair. The tissue which may be treated include epidermis, nerve, muscle, including cardiac muscle, and other tissues and wounds, and other organs such as liver, lung, cardiac, pancreas and kidney tissue. The types of wounds include, but are not limited to burns, incisions and ulcers. (See e.g., PCT Publication No. WO84/01106 for discussion of wound healing and related tissue repair). It is further contemplated that proteins of the invention may increase neuronal, astrocytic and glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, lung, cardiac, pancreas and kidney tissue. The proteins of the present invention may further be useful for the treatment of relatively undifferentiated cell populations, such as embryonic cells, or stem cells, to enhance growth and/or differentiation of the cells. The proteins of the present invention may also have value as a dietary supplement, or as a component of cell culture media. For this use, the proteins may be used in intact form, or may be predigested to provide a more readily absorbed supplement.

BMP-9 proteins of the invention may also be useful in hepatic growth and function including repair and regeneration of liver cells. BMP-9 may therefore be used for instance in treatment of conditions exhibiting degeneration of the liver.

The proteins of the invention may also have other useful properties characteristic of the TGF-β superfamily of proteins. Such properties include angiogenic, chemotactic and/or chemoattractant properties, and effects on cells including induction of collagen synthesis, fibrosis, differentiation responses, cell proliferative responses and responses involving cell adhesion, migration and extracellular matrices. These properties make the proteins of the invention potential agents for wound healing, reduction of fibrosis and reduction of scar tissue formation.

When dimerized as a homodimer or as a heterodimer with other BMPS, with other members of the TGF-β superfamily of proteins, or with inhibin-α proteins or inhibin-β proteins, the BMP-9 heterodimer is expected to demonstrate effects on the production of follicle stimulating hormone (FSH), as described further herein. It is recognized that FSH stimulates the development of ova in mammalian ovaries (Ross et al., in Textbook of Endocrinology, ed. Williams, p. 355 (1981) and that excessive stimulation of the ovaries with FSH will lead to multiple ovulations. FSH is also important in testicular function. Thus, BMP-9 may be useful as a contraceptive based on the ability of inhibins to decrease fertility in female mammals and decrease spermatogenesis in male mammals. Administration of sufficient amounts of other inhibins can induce infertility in mammals. BMP-9 may also be useful as a fertility inducing therapeutic, based upon the ability of activin molecules in stimulating FSH release from cells of the anterior pituitary. See, for example, U.S. Pat. No. 4,798,885. BMP-9 may also be useful for advancement of the onset of fertility in sexually immature mammals, so as to increase the lifetime reproductive performance of domestic animals such as cows, sheep and pigs. It is further contemplated that BMP-9 may be useful in modulating hematopoiesis by inducing the differentiation of erythroid cells [see, e.g., Broxmeyer et al, *Proc. Natl. Acad. Sci. USA*, 85:9052–9056 (1988) or Eto et al, *Biochem. Biophys. Res. Comm.*, 142:1095–1103 (1987)], for suppressing the development of gonadal tumors [see, e.g., Matzuk et al., *Nature*, 360:313–319 (1992)] or for augmenting the activity of bone morphogenetic proteins [see, e.g., Ogawa et al., *J. Biol. Chem.*, 267:14233–14237 (1992)].

BMP-9 proteins may be further characterized by their ability to modulate the release of follicle stimulating hormone (FSH) in established in vitro bioassays using rat anterior pituitary cells as described [see, e.g., Vale et al, *Endocrinology*, 91:562–572 (1972); Ling et al., *Nature*, 321:779–782 (1986) or Vale et al., *Nature*, 321:776–779 (1986)]. It is contemplated that the BMP-9 protein of the invention, when composed as a heterodimer with inhibin α or inhibin β chains, will exhibit regulatory effects, either stimulatory or inhibitory, on the release of follicle stimulating hormone (FSH), from anterior pituitary cells as described [Ling et al., *Nature*, 321:779–782 (1986) or Vale et al., *Nature*, 321:776–779 (1986); Vale et al, *Endocrinology*, 91:562–572 (1972). Therefore, depending on the particular composition, it is expected that the BMP-9 protein of the invention may have contrasting and opposite effects on the release of follicle stimulating hormone (FSH) from the anterior pituitary.

Activin A (the homodimeric composition of inhibin $β_A$) has been shown to have erythropoietic-stimulating activity [see e.g. Eto et al., *Biochem. Biophys. Res. Commun.*, 142:1095–1103 (1987) and Murata et al., *Proc. Natl. Acad. Sci. U.S.A.*, 85:2434–2438 (1988) and Yu et al., *Nature*, 330:765–767 (1987)]. It is contemplated that the BMP-9 protein of the invention may have a similar erythropoietic-stimulating activity. This activity of the BMP-9 protein may be further characterized by the ability of the BMP-9 protein to demonstrate erythropoietin activity in the biological assay performed using the human K-562 cell line as described by (Lozzio et al., *Blood*, 45:321–334 (1975) and U.S. Pat. No. 5,071,834).

BMP-9 proteins may also be useful in the regulation of lung and kidney cell function. BMP-9, or an antagonist of BMP-9, may be useful in regulating extracellular matrix components of lung and kidney in diseases in which the synthesis or degradation of extracellular matrix components is pathologic, such as emphysema and bronchitis in the lung and glomerulonephritis in the kidney. BMP-9 may also be useful as a protective or regenerative factor in acute tubular necrosis of the kidney.

A further aspect of the invention is a therapeutic method and composition for repairing fractures and other conditions related to cartilage and/or bone defects and/or other connective tissue defects or periodontal diseases. The invention further comprises therapeutic methods and compositions for wound healing and tissue repair. Such compositions comprise a therapeutically effective amount of at least one of the BMP-9 proteins of the invention in admixture with a pharmaceutically acceptable vehicle, carrier or matrix. It is expected that the proteins of the invention may act in concert with or perhaps synergistically with other related proteins and growth factors. Further therapeutic methods and compositions of the invention therefore comprise a therapeutic amount of at least one BMP-9 protein of the invention with a therapeutic amount of at least one of the other BMP proteins, BMP-1, BMP-2, BMP-3, BMP-4, BMP-5, BMP-6 and BMP-7, disclosed for instance in U.S. Pat. Nos. 5,108, 922; 5,013,649; 5,116,738; 5,106,748; 5,187,076; and 5,141, 905; BMP-8, disclosed in PCT publication WO91/18098; BMP-9, disclosed in PCT publication WO93/00432; BMP-10, disclosed in PCT application WO94/26893; BMP-11, disclosed in PCT application WO94/26892, BMP-12 or BMP-13, disclosed in PCT application WO95/16035, or BMP-15, disclosed in co-pending patent application, Ser.

No. 08/446,924, U.S. Pat. No. 5,635,372, filed on May 18, 1995. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of the above applications are hereby incorporated by reference herein. Such combinations may comprise separate molecules of the BMP proteins or heteromolecules comprised of different BMP moieties. For example, a method and composition of the invention may comprise a disulfide linked dimer comprising a BMP-9 protein subunit and a subunit from one of the "BMP" proteins described above. A further embodiment may comprise a heterodimer of BMP-9 moieties. Further, BMP-9 proteins may be combined with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), parathyroid hormone related peptide (PTHrP), leukemia inhibitory factor (LIB/HILA/DA), insulin-like growth factors (IGF-I and IFG-II). Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with BMP-9 of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than the BMP-9 proteins which may also optionally be included in the composition as described above, may alternatively or additionally, be administered simultaneously or sequentially with the BMP composition in the methods of the invention. Preferably for bone and/or cartilage formation, the composition would include a matrix capable of delivering BMP-9 or other BMP proteins to the site of bone and/or cartilage damage, providing a structure for the developing bone and cartilage and optimally capable of being resorbed into the body. The matrix may provide slow release of BMP-9 and/or the appropriate environment for presentation thereof. Such matrices may be formed of materials presently in use for other implanted medical applications.

The choice of matrix material is based on biocompatibility, biodegradability, mechanical properties, cosmetic appearance and interface properties. The particular application of the BMP-9 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-9 protein, e.g., amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), to the final composition, may also effect the dosage.

Progress can be monitored by periodic assessment of bone growth and/or repair, for example, x-rays, histomorphometric determinations and tetracycline labeling.

The following examples illustrate practice of the present invention in recovering and characterizing murine BMP-9 protein and employing it to recover the human and other BMP-9 proteins, obtaining the human proteins and expressing the proteins via recombinant techniques.

EXAMPLE I

MURINE BMP-9

750,000 recombinants of a mouse liver cDNA library made in the vector lambdaZAP (Stratagene/Catalog #935302) are plated and duplicate nitrocellulose replicas made. A fragment of human BMP-4 DNA corresponding to nucleotides 1330–1627 (SEQ ID NO:3) (the human BMP-4 sequence) is $^{32}$P-labeled by the random priming procedure of Feinberg et al., Anal. Biochem. 132:6–13 (1983) and hybridized to both sets of filters in SHB at 60° C. for 2 to 3 days. Both sets of filters are washed under reduced stringency conditions (4×SSC, 0.1% SDS at 60° C.). Many duplicate hybridizing recombinants of various intensities (approximately 92) are noted. 50 of the strongest hybridizing recombinant bacteriophage are plaque purified and their inserts are transferred to the plasmid Bluescript SK (+/−) according to the in vivo excision protocol described by the manufacturer (Stratagene). DNA sequence analysis of several recombinants indicate that they encode a protein homologous to other BMP proteins and other proteins in the TGF-β family. The DNA sequence and derived amino acid sequence of one recombinant, designated ML14a, is set forth in SEQ ID NO:1.

The nucleotide sequence of clone ML14a contains an open reading frame of 1284 bp, encoding a BMP-9 protein of 428 amino acids. The encoded 428 amino acid BMP-9 protein is contemplated to be the primary translation product as the coding sequence is preceded by 609 bp of 5' untranslated sequence with stop codons in all three reading frames. The 428 amino acid sequence predicts a BMP-9 protein with a molecular weight of 48,000 daltons.

Based on knowledge of other BMP proteins and other proteins within the TGF-β family, it is predicted that the precursor polypeptide would be cleaved at the multibasic sequence ARG-ARG-LYS-ARG amino acids #−4 to #−1 of (SEQ ID NO:1) in agreement with a proposed consensus proteolytic processing sequence of ARG-X-X-ARG amino acids #−4 to #−1 of (SEQ ID NO:1). Cleavage of the BMP-9 precursor polypeptide at this location would generate a 110 amino acid mature peptide beginning with the amino acid SER. The processing of BMP-9 into the mature form is expected to involve dimerization and removal of the N-terminal region in a manner analogous to the processing of the related protein TGF-β [L. E. Gentry et al., Mol. & Cell. Biol. 8:4162 (1988); R. Derynck et al., Nature 316:701 (1985)].

It is contemplated therefore that the mature active species of murine BMP-9 comprises a homodimer of 2 polypeptide subunits, each subunit comprising amino acids #1–#110 with a predicted molecular weight of approximately 12,000 daltons. Further active species are contemplated comprising amino acids #8–#110 thereby including the first conserved cysteine residue. As with other members of the BMP and TGF-β family of proteins, the carboxy-terminal region of the BMP-9 protein exhibits greater sequence conservation than the more amino-terminal portion. The percent amino acid identity of the murine BMP-9 protein in the cysteine-rich C-terminal domain (amino acids #8–#110) to the corresponding region of other human BMP proteins and other proteins within the TGF-β family is as follows: BMP-2, 53%; BMP-3, 43%; BMP-4, 53%; BMP-5, 55%; BMP-6, 55%; BMP-7, 53%; Vgl, 50%; GDF-1, 43%; TGF-β1, 32%; TGF-β2, 34%; TGF-β3, 34%; inhibin β(B), 34%; and inhibin β(A), 42%.

EXAMPLE II

HUMAN BMP-9

Murine and human osteoinductive factor genes are presumed to be significantly homologous, therefore the murine coding sequence or a portion thereof is used as a probe to screen a human genomic library or as a probe to identify a human cell line or tissue which synthesizes the analogous human cartilage and/or bone protein. A human genomic library (Toole et al., supra) may be screened with such a probe, and presumptive positives isolated and DNA sequence obtained. Evidence that this recombinant encodes a portion of the human BMP-9 relies of the murine/human protein and gene structure homologies.

Once a recombinant bacteriophage containing DNA encoding portion of the human cartilage and/or bone inductive factor molecule is obtained, the human coding sequence can be used as a probe to identify a human cell line or tissue which synthesizes BMP-9. Alternatively, the murine coding sequence can be used as a probe to identify such human cell line or tissue. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from a coding sequence of the murine or human BMP-9. mRNA is selected by oligo (dT) cellulose chromatography and cDNA is synthesized and cloned in lambda gt10 or lambda ZAP by established techniques (Toole et al., supra).

Additional methods known to those skilled in the art may be used to isolate the human and other species' BMP-9 proteins of the invention.

A. ISOLATION OF HUMAN BMP-9 DNA

One million recombinants of a human genomic library constructed in the vector λFIX (Stratagene catalog #944201) are plated and duplicate nitrocellulose replicas made. Two oligonucleotides probes designed on the basis of nucleotides #1665–#1704 and #1837–#1876 of SEQ ID NO:1 are synthesized on an automated DNA synthesizer. The sequence of these two oligonucleotides is indicated below:

1: CTATGAGTGTAAAGGGGGTTGCTTCTTC-CCATTGGCTGAT

2: GTGCCAACCCTCAAGTACCACTAT-GAGGGGATGAGTGTGG

These two oligonucleotide probes are radioactively labeled with $\gamma^{32}$P-ATP and each is hybridized to one set of the duplicate nitrocellulose replicas in SHB at 65° C. and washed with 1×SSC, 0.1% SDS at 65° C. Three recombinants which hybridize to both oligonucleotide probes are noted. All three positively hybridizing recombinants are plaque purified, bacteriophage plate stocks are prepared and bacteriophage DNA is isolated from each. The oligonucleotide hybridizing regions of one of these recombinants, designated HGlll, is localized to a 1.2 kb Pst I/Xba I fragment. This fragment is subcloned into a plasmid vector (pGEM-3) and DNA sequence analysis is performed. HG111 was deposited with the American Type Culture Collection ATCC, 12301 Parklawn Drive, Rockville, Md. USA (hereinafter the "ATCC") on Jun. 16, 1992 under the requirements of the Budapest Treaty and designated as ATCC #75252. This subclone is designated pGEM-111. A portion of the DNA sequence of clone pGEM-111 is set forth in SEQ ID NO:8/HUMAN BMP-9 SEQUENCE. This sequence encodes the entire mature region of human BMP-9 and a portion of the propeptide. It should be noted that this sequence consists of preliminary data. Particularly, the propeptide region is subject to further analysis and characterization. For example, nucleotides #1 through #3 (TGA) encode a translational stop which may be incorrect due to the preliminary nature of the sequence. It is predicted that additional sequences present in both pGEM-111 (the 1.2 kb PstI/XbaI fragment of HG111 subcloned into PGEM) and HG111 encode additional amino acids of the human BMP-9 propeptide region. Based on knowledge of other BMPs and other proteins within the TGF-β family, it is predicted that the precursor polypeptide would be cleaved at the multibasic sequence ARG-ARG-LYS-ARG (amino acids #−4 through #−1 of SEQ ID NO:9) in agreement with a proposed consensus proteolytic processing sequence ARG-X-X-ARG amino acids #−4 to #−1 of (SEQ ID NO:1). Cleavage of the human BMP-9 precursor polypeptide at this location would generate a 110 amino acid mature peptide beginning with the amino acid SER at position #1 of SEQ ID NO:9 (encoded by nucleotides #124 through #126 of SEQ ID NO:8). The processing of human BMP-9 into the mature form is expected to involve dimerization and removal of the N-terminal region in a manner analogous to the processing of the related protein TGF-β [L. E. Gentry et al., Mol. & Cell. Biol. 8:4162 (1988); R. Derynck et al., Nature 316:701 (1985)].

It is contemplated therefore that the mature active species of human BMP-9 comprises a homodimer of two polypeptide subunits, each subunit comprising amino acids #1 through #110 of SEQ ID NO:9, with a predicted molecular weight of 12,000 daltons. Further active species are contemplated comprising amino acids #8 through #110 thereby including the first conserved cysteine residue. As with other members of the BMP and TGF-β family of proteins, the carboxy-terminal portion of the human BMP-9 sequence exhibits greater sequence conservation than the amino-terminal portion. The percent amino acid identity of the human BMP-9 protein in the cysteine-rich C-terminal domain (amino acids #8 through #110) to the corresponding region of other human BMP proteins and other proteins within the TGF-β family is as follows: BMP-2, 52%; BMP-3, 40%; BMP-4, 52%; BMP-5, 55%; BMP-6, 55%; BMP-7, 53%; murine BMP-9, 97%; Vgl, 50%; GDF-1, 44%; TGF-β1, 32%; TGF-β2, 32%; TGF-β3, 32%; inhibin β (B), 35%; and inhibin β (A), 41%. BMP-9 exhibits 80% homology to chick Dorsalin-1, a BMP-like protein cloned from embryonic chick.

EXAMPLE III
ROSEN MODIFIED SAMPATH-REDDI ASSAY

A modified version of the rat bone formation assay described in Sampath and Reddi, Proc. Natl. Acad. Sci. USA 80:6591–6595 (1983) is used to evaluate bone and/or cartilage activity of the BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [See, A. H. Reddi et al., Proc. Natl Acad Sci. 69:1601 (1972)].

The other half of each implant is fixed and processed for histological analysis. llm glycolmethacrylate sections are stained with Von Kossa and acid fuschin to score the amount of induced bone and cartilage formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2 and +1 would indicate that greater than 406, 30%, 20% and 10% respectively of the implant contains new cartilage and/or bone. In a modified scoring method, three non-adjacent sections are evaluated from each implant and averaged. "+/−" indicates tentative identification of cartilage or bone; "+1" indicates >10% of each section being new cartilage or bone; "+2", >25%; "+3", >50%; "+4", ~75%; "+5", >80%. A "−" indicates that the implant is not recovered.

It is contemplated that the dose response nature of the BMP-9 containing samples of the matrix samples will demonstrate that the amount of bone and/or cartilage formed increases with the amount of BMP-9 in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV
EXPRESSION OF BMP-9

In order to produce murine, human or other mammalian BMP-9 proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-9 is contemplated to be stably transformed mammalian cells.

One skilled in the art can construct mammalian expression vectors by employing the sequence of SEQ ID NO:1 or SEQ ID NO:8, or other DNA sequences encoding BMP-9 proteins or other modified sequences and known vectors, such as pCD [Okayama et al., Mol. Cell Biol. 2:161–170 (1982)], pJL3, pJL4 [Gough et al., EMBO J. 4:645–653 (1985)] and pMT2 CXM.

The mammalian expression vector pMT2 CXM is a derivative of p91023 (b) (Wong et al., Science 228:810–815 (1985)) differing from the latter in that it contains the ampicillin resistance gene in place of the tetracycline resistance gene and further contains a XhoI site for insertion of cDNA clones. The functional elements of pMT2 CXM have been described (Kaufman, R. J., Proc. Natl. Acad. Sci. USA 82:689–693 (1985)) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC #67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga et al., Biotechnology 84:636 (1984)]. This removes bases 1075 to 1145 relative to the Hind III site near the SV40 origin of replication and enhancer sequences of pMT2. In addition it inserts the following sequence:

5' PO-CATGGGCAGCTCGAG-3' (SEQ ID NO:5) at nucleotide 1145. This sequence contains the recognition site for the restriction endonuclease Xho I. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2bl derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E. coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'

(SEQ ID NO:6)
5' -CTGCAGGCGAGCCTGAATTCCTCGAGCCATCATG-3'
    PstI        Eco RI XhoI (SEQ ID NC:6)
Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B1.

A portion of the EMCV leader is obtained from pMT2-ECAT1 [S. K. Jung et al., J. Virol 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

5'-CGAGGTTAAAAAACGTCTAGGCCCCCCGAACC
       ACGGGGACGTGGTTTTCCTTT
       TaqI
    GAAAAACACGATTGC-3'
       XhoI (SEQ ID NO:7)

This sequence matches the EMC virus leader sequence from nucleotide 763 to 827. It also changes the ATG at position 10 within the EMC virus leader to an ATT and is followed by a XhoI site. A three way ligation of the pMT21 Eco RI-XhoI fragment, the EMC virus EcoRI-TaqI fragment, and the 68 bp oligonucleotide adapter TaqI-XhoI adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-9 DNA sequences. For instance, BMP-9 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-9 proteins. One skilled in the art can manipulate the sequences of SEQ ID NOS:1 and 8 by eliminating or replacing the mammalian regulatory sequences flanking the coding sequence with bacterial sequences to create bacterial vectors for intracellular or extracellular expression by bacterial cells. For example, the coding sequences could be further manipulated (e.g., ligated to other known linkers or modified by deleting non-coding sequences therefrom or altering nucleotides therein by other known techniques). The modified BMP-9 coding sequence could then be inserted into a known bacterial vector using procedures such as described in T. Taniguchi et al., Proc. Natl Acad. Sci. USA 77:5230–5233 (1980). This exemplary bacterial vector could then be transformed into bacterial host cells and a BMP-9 protein expressed thereby. For a strategy for producing extracellular expression of BMP-9 proteins in bacterial cells, see e.g., European Patent Application No. EPA 177,343.

Similar manipulations can be performed for the construction of an insect vector [See e.g., procedures described in published European Patent Application No. 155,476] for expression in insect cells. A yeast vector could also be constructed employing yeast regulatory sequences for intracellular or extracellular expression of the factors of the present invention by yeast cells. [See e.g., procedures described in published PCT Publication No. WO86/00639 and European Patent Application No. EPA 123,289].

A method for producing high levels of a BMP-9 protein of the invention in mammalian cells may involve the construction of cells containing multiple copies of the heterologous BMP-9 gene. The heterologous gene is linked to an amplifiable marker, e.g., the dihydrofolate reductase (DHFR) gene for which cells containing increased gene copies can be selected for propagation in increasing concentrations of methotrexate (MTX) according to the procedures of Kaufman and Sharp, J. Mol. Biol. 159:601–629 (1982). This approach can be employed with a number of different cell types.

For example, a plasmid containing a DNA sequence for a BMP-9 of the invention in operative association with other plasmid sequences enabling expression thereof and the DHFR expression plasmid pAdA26SV(A)3 [Kaufman and Sharp, Mol. Cell. Biol. 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g., sequential steps in 0.02, 0.2, 1.0 and 5uM MTX) as described in Kaufman et al., Mol Cell Biol. 5:1750 (1983). Transformants are cloned, and biologically active BMP-9 expression is monitored by the Rosen-modified Sampath-Reddi rat bone formation assay described above in Example III. BMP-9 expression should increase with increasing levels of MTX resistance. BMP-9 polypeptides are characterized using standard techniques known in the art such as pulse labeling with [35S] methionine or cysteine and polyacrylamide gel electrophoresis. Similar procedures can be followed to produce other related BMP-9 proteins.

A. BMP-9 VECTOR CONSTRUCTION

In order to produce human BMP-9 proteins of the invention DNA sequences encoding the mature region of the human BMP-9 protein may be joined to DNA sequences encoding the propeptide region of the murine BMP-9 protein. This murine/human hybrid DNA sequence is inserted into an appropriate expression vector and introduced into mammalian cells or other preferred eukaryotic or prokaryotic hosts by conventional genetic engineering techniques. The construction of this murine/human BMP-9 containing expression plasmid is described below.

A derivative of the human BMP-9 sequence (SEQ ID NO:8) comprising the nucleotide sequence from nucleotide #105 to #470 is specifically amplified. The following oligonucleotides are utilized as primers to allow the amplification of nucleotides #105 to #470 of the human BMP-9 sequence (SEQ ID NO:8) from clone pGEM-111 described above.

3     ATCGGGCCCCTTTTAGCCAGGCG-
       GAAAAGGAG (SEQ ID NO: 10)
   #4  AGCGAATTCCCCGCAGGCAGATACTACCTG
      (SEQ ID NO: 11)

This procedure generates the insertion of the nucleotide sequence ATCGGGCCCCT immediately preceding nucleotide #105 and the insertion of the nucleotide sequence GAATTCGCT immediately following nucleotide #470. The addition of these sequences results in the creation of an Apa I and EcoR I restriction endonuclease site at the respective ends of the specifically amplified DNA fragment. The resulting 374 bp Apa I/EcoR I fragment is subcloned into the plasmid vector pGEM-7Zf (+) (Promega catalog# p2251) which has been digested with Apa I and EcoR I. The resulting clone is designated phBMP9mex-1.

The following oligonucleotides are designed on the basis of murine BMP-9 sequences (SEQ ID NO:1) and are modified to facilitate the construction of the murine/human expression plasmid referred to above:

```
#5  GATTCCGTCGACCACCATGTCCCCTGGGGCCTGGTCTAGATGGATACACAGCTGTGGGCC    (SEQ ID NO: 12)

#6  CCACAGCTGTGTATCCATCTAGACCAGGCCCCAGGGGACATGGTGGTCGACG            (SEQ ID NO: 13)
```

These oligonucleotides contain complimentary sequences which upon addition to each other facilitate the annealing (base pairing) of the two individual sequences, resulting in the formation of a double stranded synthetic DNA linker (designated LINK-1) in a manner indicated below:

```
      1   5    10        20        30        40        50        60
      |   |    |         |         |         |         |         |
#5  GATTCCGTCGACCACCATGTCCCCTGGGGCCTGGTCTAGATGGATACACAGCTGTGGGCC    (SEQ ID NO: 14)
        GCTGGTGGTACAGGGGACCCCGGACCAGATCTACCTATGTGTCGACACC #6          (SEQ ID NO: 15)
```

This DNA linker (LINK-1) contains recognition sequences of restriction endonucleases needed to facilitate subsequent manipulations required to construct the murine/human expression plasmid, as well as sequences required for maximal expression of heterologous sequences in mammalian cell expression systems. More specifically (referring to the sequence numbering of oligonucleotide #5/LINK-1): nucleotides #1–#11 comprise recognition sequences for the restriction endonucleases BamH I and Sal I, nucleotides #11–#15 allow for maximal expression of heterologous sequences in mammalian cell expression systems, nucleotides #16–#31 correspond to nucleotides #610–#625 of the murine BMP-9 sequence (SEQ ID NO:1), nucleotides #32–#33 are inserted to facilitate efficient restriction digestion of two adjacent restriction endonuclease sites (EcoO109 I and Xba I), nucleotides #34–#60 correspond to nucleotides #1515–#1541 of the murine BMP-9 sequence (SEQ ID NO:1) except that nucleotide #58 of synthetic oligonucleotide #5 is a G rather than the A which appears at position #1539 of SEQ ID NO:1 (This nucleotide conversion results in the creation of an Apa I restriction endonuclease recognition sequence, without altering the amino acid sequence it is intended to encode, to facilitate further manipulations of the murine/human hybrid expression plasmid. LINK-1 (the double stranded product of the annealing of oligonucleotides #5 and #6) is subcloned into the plasmid vector pGEM-7Zf (+) which has been digested with the restriction endonucleases Apa I and BamH I. This results in a plasmid in which the sequences normally present between the Apa I and BamH I sites of the pGEM-7Zf(+) plasmid polylinker are replaced with the sequences of LINK-1 described above. The resulting plasmid clone is designated pBMP-9link.

pBMP-9link is digested with the restriction endonucleases BamH I and Xba I resulting in the removal nucleotides #1–#34 of LINK-1 (refer to the numbering of oligo #5). Clone ML14a, which contains an insert comprising the sequence set forth in SEQ ID NO:1,is also digested with the restriction endonucleases BamH I and Xba I resulting in the removal of sequences comprising nucleotides #1–#1515 of SEQ ID NO:1 (murine BMP-9). This BamH I/Xba I fragment of mouse BMP-9 is isolated from the remainder of the ML14a plasmid clone and subcloned into the BamH I/Xba I sites generated by the removal of the synthetic linker sequences described above. The resulting clone is designated p302.

The p302 clone is digested with the restriction endonuclease EcoO109 I resulting in the excision of nucleotides corresponding to nucleotides #621–#1515 of the murine BMP-9 sequence (SEQ ID NO:1) and nucleotides #35–#59 of LINK-1 (refer to numbering of oligonucleotide #5). It should be noted that the Apa I restriction site created in LINK-1 by the A to G conversion described above is a subset of the recognition sequence of EcoO109 I, therefore digestion of p302 with EcoO109 I cleaves at the Apa I site as well as the naturally occurring murine EcoO109 I (location #619–#625 of SEQ ID NO:1) resulting in the excision of a 920 bp EcoO109 I/EcoO109 I (Apa I) fragment comprising the sequences described above. This 920 EcoO109 I/EcoO109 I (Apa I) fragment is isolated from the remainder of the p302 plasmid clone and subcloned into clone pBMP-9link which has been similarly digested with EcoO109 I. It should be noted that the nucleotides GG (#32–#33 of oligonucleotide #5) originally designed to facilitate a more complete digestion of the two adjacent restriction sites EcoO109 I and Xba I of LINK-1, which is now a part of pBMP-9link (described above), results in the creation of Dcm methylation recognition sequence. The restriction nuclease EcoO109 I is sensitive to Dcm methylation and therefore cleavage of this sequence (nucleotides #25–#31 of oligonucleotide #5/LINK-1) by the restriction endonuclease EcoO109 I is prevented at this site. Therefore the plasmid clone pBMP-9link is cleaved at the Apa I site but not at the EcoO109 I site upon digestion with the restriction endonuclease EcoO109 I as described above, preventing the intended removal of the sequences between the EcoO109 I and Xba I site of LINK-1 (#32–#55 defined by the numbering of oligonucleotide #5). This results in the insertion of the 920 bp EcoO109 I/Apa I fragment at the EcoO109 I (Apa I) site of pBMP-9link. The resulting clone is designated p318.

Clone p318 is digested with the restriction endonucleases Sal I and Apa I, resulting in the excision of sequences comprising nucleotides #6–#56 of LINK-1 (refer to oligo #5 for location), nucleotides #621–#1515 of murine BMP-9 (SEQ ID NO:1), and nucleotides #35–#60 of LINK-1 (refer to oligo #5 for location). The resulting 972 bp Sal I/Apa I fragment described above is isolated from the remainder of the p318 plasmid clone and will be utilized in subsequent manipulations.

The clone phBMP9mex-1 (described above), which contains DNA Th; sequences which encode the entire mature region and portions of the propeptide of the human BMP-9 protein, is digested with the restriction endonucleases Apa I and EcoR I. This results in the excision of a 374 bp fragment comprising nucleotides #105–#470 of the human BMP-9 sequence (SEQ ID NO:8) and the additional nucleotides of oligonucleotide primers #3 and #4 which contain the recognition sequences for the restriction endonucleases Apa I and EcoR I. This 374 bp Apa I/EcoR I fragment is combined with the 972 bp Sal I/Apa I fragment from p138 (isolation described above) and ligated to the mammalian cell expression plasmid pED6 (a derivative of pEMC2β1) which has been digested with Sal I and EcoR I. The resulting clone is designated p324.

The clone ML14a (murine BMP-9) is digested with EcoO109 I and Xba I to generate a fragment comprising nucleotides #621–#1515 of SEQ ID NO:1.

The following oligonucleotides are synthesized on an automated DNA synthesizer and combined such that their complimentary sequences can base pair (anneal) with each other to generate a double stranded synthetic DNA linker designated LINK-2:

7 TCGACCACCATGTCCCCTGG (SEQ ID NO: 16)
8 GCCCCAGGGGACATGGTGG (SEQ ID NO: 17)

This double stranded synthetic DNA linker (LINK-2) anneals in such a way that it generates single stranded ends which are compatible to DNA fragments digested with Sal I (one end) or EcoO109 I (the other end) as indicated below:

7 TCGACCACCATGTCCCCTGG (SEQ ID NO: 18)
GGTGGTACAGGGGACCCCG #8 (SEQ ID NO: 19)

This LINK-2 synthetic DNA linker is ligated to the 895 bp EcoO109 I/Xba I fragment comprising nucleotides #621–#1515 of murine BMP-9 (SEQ ID NO:1) described above. This results in a 915 bp Sal I/Xba I fragment.

The clone p324 is digested with Sal I/Xba I to remove sequences comprising nucleotides #6–#56 of LINK-1 (refer to oligo #5 for location) and nucleotides #621–#1515 of murine BMP-9 (SEQ ID NO:1). The sequences comprising nucleotides #35–#60 of LINK-1 (refer to oligo #5 for location) and the sequences comprising the 374 bp Apa I/EcoR I fragment (human BMP-9 sequences) derived from phBMP9mex-1 remain attached to the pED6 backbone. The 915 bp Sal I/Xba I fragment comprising LINK-2 sequences and nucleotides #621–#1515 of murine BMP-9 (SEQ ID NO:1) is ligated into the p324 clone from which the Sal I to Xba I sequences described above have been removed.

The resulting plasmid is designated BMP-9 fusion and comprises LINK-2, nucleotides #621–#1515 of murine BMP-9 (SEQ ID NO:1), nucleotides #35–#59 of LINK-1 (refer to the numbering of oligonucleotide #5), and the 374 bp Apa I/EcoR I fragment (human BMP-9) derived from clone pBMP9mex-1 (described above) inserted between the Sal I and EcoR I sites of the mammalian cell expression vector pED6.

B. EXPRESSION

BMP-9 fusion is transfected into CHO cells using standard techniques known to those having ordinary skill in the art to create stable cell lines capable of expressing human BMP-9 protein. The cell lines are cultured under suitable culture conditions and the BMP-9 protein is isolated and purified from the culture medium.

In one embodiment, cells are grown in R1 medium based on a 50:50 mix of F12 and DME plus extra non-essential amino acids plus extra biotin and B12 and 100i fetal bovine serum (FBS) and 0.2 $\mu$M methotrexate (MTX). Cells are grown up and expanded into roller bottles in this medium using confluent roller bottles. The serum containing growth medium is discarded, the rollers are rinsed with PBS-CMF, and a serum free production medium is added containing additional amino acids plus insulin (5 $\mu$g/ml), putrescine (12.9 $\mu$M), hydrocortisone (0.2 $\mu$M), selenium (29 nM), and PVA (0.6 g/L). Dextran sulfate is used in this CM (at 100 $\mu$g/ml). Conditioned medium (CM) is collected at 24 hours and the rollers are refed with fresh serum free medium. Four sequential 24 hour harvest can be collected. Conditioned medium is clarified (floating cells in the CM are removed) for purification by passing the CM through a 5$\mu$ (pass Profile) pore size filter and a 0.22$\mu$ (millipore Duropore) pore size filter.

EXAMPLE V
BIOLOGICAL ACTIVITY OF EXPRESSED BMP-9

To measure the biological activity of the expressed BMP-9 proteins obtained in Example IV above, the proteins are recovered from the cell culture and purified by isolating the BMP-9 proteins from other proteinaceous materials with which they are co-produced as well as from other contaminants. The purified protein may be assayed in accordance with the rat bone formation assay described in Example III.

Purification is carried out using standard techniques known to those skilled in the art. It is contemplated, as with other BMP proteins, that purification may include the use of Heparin sepharose.

In one embodiment, 40 liters of the conditioned media from Example IV-B is titrated to pH 6.9 with concentrated sodium phosphate pH 6.0, and loaded onto Cellufine Sulfate, previously equilibrated with 50 mM sodium phosphate, pH 6.9. The resin is washed with 50 mM sodium phosphate, 0.5 M NaCl, followed by 50 mM sodium phosphate, 0.5 M NaCl, 0.5 M Arg, pH 6.9. BMP-9 is found in the wash as well as the elution, with a lesser amount of contaminants in the elution pool. Cellufine sulfate pools are concentrated and directly loaded onto RP-HPLC for final purification. Each concentrated pool is titrated to pH 3.8 with dilute TFA and loaded onto a 0.46×25 cm $C_4$ reverse phase column running a linear gradient from 30% A (0.1% TFA/$H_2$O) to 55% B (0.1% TFA/90% Acetonitrile) over 100 minutes. BMP-9 monomer is separated by baseline resolution from BMP-9 dimer. The identity of monomer and dimer pools are confirmed by N-terminal sequencing. Although heterogeneity in the N-terminus is expected sequencing reveals a predominant species Ser-Ala-Gly-Ala beginning with amino acid #1 of SEQ ID NO:9.

Protein analysis is conducted using standard techniques such as SDS-PAGE acrylamide [U. K. Laemmli, Nature 227:680 (1970)] stained with silver [R. R. Oakley et al., Anal. Biochem. 105:361 (1980)] and by immunoblot [H. Towbin et al., Proc. Natl. Acad. Sci. USA 76:4350 (1979)]. BMP-9 is efficiently expressed in CHO cells as a 14kDa nonglycosylated protein when analyzed under reducing conditions. BMP-9 is efficiently secreted within 4 hours of its synthesis.

EXAMPLE VI
A. W-20 BIOASSAY

Use of the W-20 bone marrow stromal cells as an indicator cell line is based upon the conversion of these cells to osteoblast-like cells after treatment with BMP-2 [R. S. Thies et al., "Bone Morphogenetic Protein alters W-20 stromal cell differentiation in vitro", *Journal of Bone and Mineral Research* 5(2):305 (1990); and R. S. Thies et al., "Recombinant Human Bone Morphogenetic Protein 2 Induces Osteoblastic Differentiation in W-20–17 Stromal Cells", *Endocrinology*, 130(3):1318–1324 (1992)]. Specifically, W-20 cells are a clonal bone marrow stromal cell line derived from adult mice by researchers in the laboratory of Dr. D. Nathan, Children's Hospital, Boston, Mass. BMP-2 treatment of W-20 cells results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 ALKALINE PHOSPHATASE ASSAY PROTOCOL

W-20 cells are plated into 96 well tissue culture plates at a density of 10,000 cells per well in 200 $\mu$l of media (DME with 10% heat inactivated fetal calf serum, 2 mM glutamine and 100 U/ml+100 $\mu$g/ml streptomycin. The cells are allowed to attach overnight in a 95% air, 5% $CO_2$ incubator at 37° C.

The 200 $\mu$l of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate.

The test samples and standards are allowed a 24 hour incubation period with the W-20 indicator cells. After the 24 hours, plates are removed from the 37° C. incubator and the test media are removed from the cells.

The W-20 cell layers are washed 3 times with 200 $\mu$l per well of calcium/magnesium free phosphate buffered saline and these washes are discarded.

50 $\mu$l of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement.

50 $\mu$l of assay mix (50 mM glycine, 0.05% Triton X-100, 4 mM $MgCl_2$, 5 mM p-nitrophenol phosphate, pH=10.3) is added to each assay well and the assay plates are then incubated for 30 minutes at 37° C. in a shaking waterbath at 60 oscillations per minute.

At the end of the 30 minute incubation, the reaction is stopped by adding 100 $\mu$l of 0.2 N NaOH to each well and placing the assay plates on ice.

The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

| Absorbance Values for Known Standards of P-Nitrophenol Phosphate | |
| --- | --- |
| P-nitrophgenol phosphate umoles | Mean Absorbance (405 nm) |
| 0.000 | 0 |
| 0.006 | 0.261 ± .024 |

TABLE I-continued

| Absorbance Values for Known Standards of P-Nitrophenol Phosphate | |
| --- | --- |
| P-nitrophgenol phosphate umoles | Mean Absorbance (405 nm) |
| 0.012 | 0.521 ± .031 |
| 0.018 | 0.797 ± .063 |
| 0.024 | 1.074 ± .061 |
| 0.030 | 1.305 ± .083 |

Absorbance values for known amounts of BMP-2 can be determined and converted to $\mu$moles of p-nitrophenol phosphate cleaved per unit time as shown in Table II.

TABLE II

| Alkaline Phosphatase Values for W-20 Cells Treating with BMP-2 | | |
| --- | --- | --- |
| BMP-2 concentration ng/ml | Absorbance Reading 405 nmeters | umoles substrate per hour |
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-9 to BMP-2.

C. OSTEOCALCIN RIA PROTOCOL

W-20 cells are plated at $10^6$ cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C.

The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias.

At. the end of 96 hours, 50 $\mu$l of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 include osteocalcin synthesis by W-20 cells are shown in Table III.

TABLE III

Osteocalcin Synthesis by W-20 Cells

| BMP-2 Concentration ng/ml | Osteocalcin synthesis ng/well |
| --- | --- |
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

EXAMPLE VII
ARTICULAR CARTILAGE ASSAY

The effect of BMP-9 on articular cartilage proteoglycan and DNA synthesis is assayed to determine if BMP-9 is involved in the regulation of metabolism of differentiated articular cartilage.

Articular cartilage explants from calf carpal joints are maintained in DMEM with 50 µg/ml ascorbate, 4 mM glutamine and antibiotics for 3 days. Cytokines (rhBMP-2, rhBMP-4, rhBMP-6 and rhBMP-9, IGF-1, bFGF (1–1000 ng/ml), and TGFβ (1–100 ng/ml)) are added to the medium and culture is continued for 3 more days. Medium is changed daily. Twenty-four hours prior to harvest, explants are pulsed with 50 µCi/ml $^{35}SO_4$ or 25 µCi/ml $^3$H-thymidine. Explants are solubilized and separation of free isotope is performed by gel chromatography. Total DNA of each explant is measured by a spectrophotometric assay. BMP-9 stimulates proteoglycan synthesis above control levels at a dose of 10 ng/ml (p<0.05).

BMP-4, BMP-6, BMP-9 and TGFβ are significantly more active in stimulating proteoglycan synthesis at 100 ng/ml. At the highest doses of cytokine tested (1 µg/ml), proteoglycan synthesis by explants exposed to all cytokines are significantly greater (p<0.05) than that by control explants. Sulfate incorporation results are set forth in FIG. 1.

Recombinant human BMP-9 stimulates alkaline phosphatase activity in the osteoprogenitor cell line, W-20–17, in a dose responsive manner with an $ED_{50}$ of 4 ng/ml. In vivo, high doses in rhBMP-9 induce ectopic bone formation, with 25 µg/implant of rhBMP-9 inducing cartilage and bone tissue after 10 days of implantation.

EXAMPLE VIII
STIMULATION OF LIVER CELLS

It is contemplated that BMP-9 may be used in liver repair or regeneration. Through the use of whole embryo sections or whole mount techniques, expression of mRNA in multiple tissue is screened simultaneously. In the 11.5 dpc mouse embryo, BMP-9 mRNA localizes exclusively to the developing liver. It is contemplated that BMP-9, like all other BMPs studied to date, acts as a local regulator of cell growth and differentiation, therefore this very specific expression pattern suggests liver as a BMP-9 target tissue.

Figure 2:
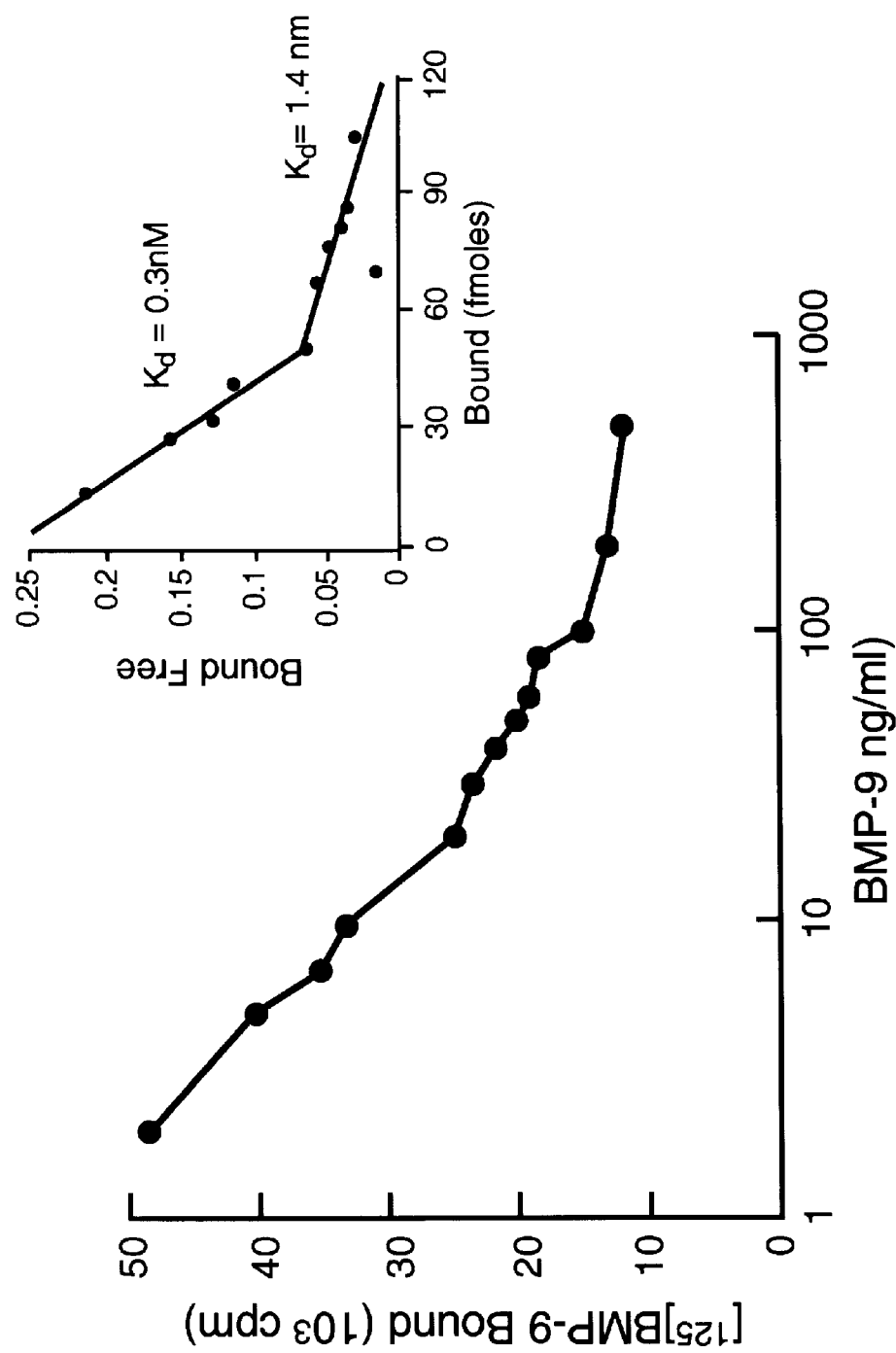
FIG. 2 sets forth results of specific BMP-9 binding to HepG2 cells.

BMP-9 responsiveness in parenchymal liver cells is tested by screening four liver cell lines for their ability to bind iodinated, CHO-derived BMP-9. The four liver cell lines, HepG2 (ATCC HB8065), NMuli (ATCC CRL1638), Chang and NCTC1469 (ATCC CCL9.1), all specifically bind $^{125}$I-BMP-9 to some extent, with HepG2 and NCTC1469 cell lines exhibiting the highest degree of binding. Specific binding of BMP-9 to HepG2 cells is carried out by incubating HepG2 cells grown to confluence in Dulbecco's Modified Eagle's Medium (DME) containing 10% heat-inactivated fetal calf serum (FCS) on gelatinized 6 well plates with 2 ng/ml $^{125}$I-BMP-9 and increasing concentrations of unlabelled BMP-9 in binding buffer (136.9 mM NaCl, 5.37 mM KCl, 1.26 mM $CaCl_2$, 0.64 mM $MgSO_4$, 0.34 mM $Na_2HPO_4$, 0.44 mM $KH_2PO_4$, 0.49 mM $MgCl_2$, 25 mM HEPES and 0.5% BSA, pH 7.4) for 20 hours at 4° C. to achieve binding equilibrium. This incubation follows a one hour preincubation at 37° C. in binding buffer alone. For crosslinking experiments, the cells were incubated with 500 µM disuccinimidyl suberate for 20 minutes at 40° C. following binding. Cell extracts were analyzed on SDS-PAGE. As shown in FIG. 2, HepG2 cells expressed abundant high affinity receptors for BMP-9. Scatchard analysis of these binding data resulted in a curvilinear plot, with approximately 10,000 high affinity receptors per cell. These receptors exhibited a $K_d$ of 0.3 nM. The curvilinear nature of the Scatchard plot indicates negative cooperativity among BMP-9 receptors or that HepG2 cells express at least two populations of BMP-9 receptors with different affinities. Crosslinking analysis on HepG2 cells with $^{125}$I-BMP-9 yields two binding proteins of apparent molecular weights of 54 and 80 kD. Crosslinked ligand/receptor complexes were observed at 78 and 100 kD under nonreducing conditions, and 67 and 94 kD under reducing conditions. Subtracting the molecular weight of the BMP-9 dimer and monomer, respectively, it is estimated that these BMP-9 receptor proteins have molecular weights of approximately 54 and 80 kD. The $K_d$ of the high affinity binding sites for BMP-9 is estimated to be approximately 270 pM for HepG2 cells. To test the binding specificity of the receptors for BMP-9, HepG2 cells were incubated with $^{125}$I-BMP-9 and a 250-fold excess of different unlabeled ligands. The BMP-9 receptors expressed on HepG2 cells show only limited crossreactivity with BMPs 2 and 4, and no crossreactivity with BMPs 3, 5, 6, 7, 12 and 2/6, or with TGF-β1 or TGF-β2.

As a first indication of BMP-9 effects on confluent, serum starved HepG2 cells, cell proliferation is examined as determined by $^3$H-thymidine incorporation and cell counting. HepG2 cells are plated at $10^6$ cells/well in 96 well plates and cultured for 48 hours in DME/0.1% FCS to synchronize the cell cycle are treated for 24 hours with or without BMP-9 in the presence of 0.1% FCS. In $^3$H-thymidine incorporation assays, $^3$H-thymidine was included during the last 4 hours of treatment and cellular DNA was collected with a 96 well plate cell harvester. Proliferation was assayed by quantifying ethanol-precipitable $^3$H-thymidine incorporation by liquid scintillation counting. For cell counting assays, cells were trypsinized and counted with a hemacytometer. Primary rat hepatocytes isolated from male Fischer 344 rats (Charles River, Wilmington, Mass.) by collagenase digestion as previously described [Michalopoulos et al., Cancer Res. 42:4673–4682 (1982)] are plated on collagen-coated plates at subconfluence (5,000–10,000 cells/cm$^2$) in serum-free media as described in Michalopoulos et al., Cancer Res. 42:4673–4682 (1982) and treated with or without rhBMP-9 for 36 hours. $^3$H-thymidine was included throughout the treatment period and incorporated $^3$H-thymidine was quantified as described by Anscher et al., New England J. Med. 328:1592–1598 (1993). BMP-9 stimulates $^3$H-thymidine incorporation in HepG2 cells approximately five fold. This effect is confirmed by a stimulatory effect of BMP-9 in cell counting experiments. As shown in FIG. 3, BMP-9 stimulated $^3$H-thymidine incorporation in HepG2 cells in a dose-responsive manner. The ED$_{50}$ for this effect was estimated at 10 ng/ml BMP-9. This ED$_{50}$ value is consistent with the estimated binding affinity (K$_d$=0.3 nM=8 ng/ml), suggesting that this biological effect is mediated by the described BMP-9 receptors.

Figure 4:
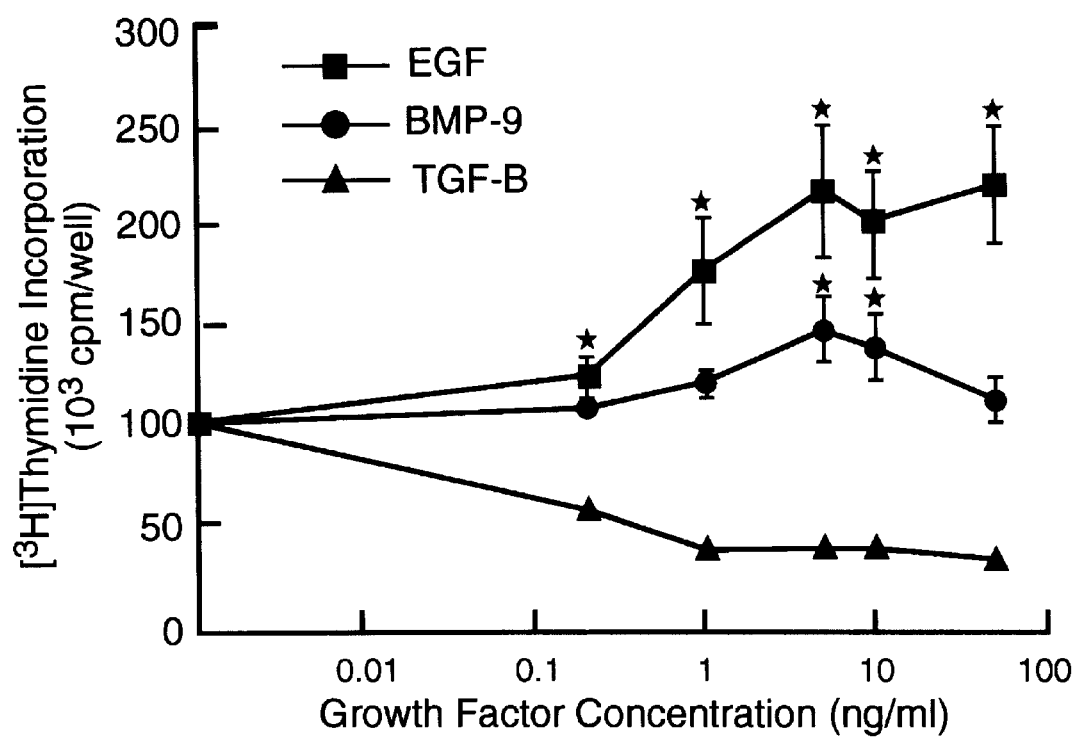
FIG. 4 sets forth the results of stimulation of primary rat hepatocytes by BMP-9.

To determine if this proliferative effect of BMP-9 was unique to the HepG2 liver tumor cell line, primary rat hepatocytes were tested for effects of BMP-9 on $^3$H-thymidine incorporated as shown in FIG. 4. BMP-9 stimulated $^3$h-thymidine incorporation in primary hepatocytes, although not as markedly as EGF. This stimulatory effect is cell density-dependent in primary rat hepatocytes. While subconfluent cells exhibited a stimulation in response to BMP-9, confluent primary hepatocytes did not. As indicated in FIG. 4, in contrast to rhBMP-9, TGF-β1 was inhibitory, not stimulatory on primary rat hepatocytes.

EXAMPLE IX
BMP-9 TARGET TISSUES

To determine potential target tissues for BMP-9, plasma membrane preparations from adult rat organs are screened for specific [$^{125}$I]rhBMP-9 binding. Plasma membranes are prepared by the methods of Neville, *J. Biophys Biochem Cytol* 8:412–422 (1960) and Ray, *Biochim Biophys Acta* 196:1–9 (1970) with the following modifications: Fresh tissues from adult male Long-Evans rats are homogenized with 10 strokes of a teflon homogenizer. Plasma membranes are collected from discontinuous sucrose gradients at 37%/41% sucrose interface and the 41%/45% sucrose interface. Homogenization buffer and sucrose solutions are supplemented with 0.7 μg/ml leupeptin, 2 μg/ml aprotinin and 240 μg/ml pefabloc. Protein levels in plasma membrane preparations are determined by the bicinchoninic acid assay (Pierce, Rockford, Ill.) using immunoglobulin G as a standard.

BMP-9 binding is carried out by suspending plasma membranes at 30 μg/100μl in binding buffer (136.9 mM NaCl, 5.37 mM KCl, 1.26 mM CaCl$_2$, 0.64 mM MgSO$_4$, 0.34 mM Na$_2$HPO$_4$, 0.44 mM KH$_2$PO$_4$, 0.49 mM MgCl$_2$, 25 mM HEPES and 0.5% BSA, pH 7.4) containing o.5 ng [$^{125}$I]rhBMP-9. Binding is allowed to equilibrate by incubation for 16 h at 4° C. After the incubation period, membranes are pelleted by centrifugation at 13,000 g for 3 min, and washed three times with ice-cold binding buffer, before quantitation in a gamma counter. rhBMP-9 is iodinated to a specific activity of 50–100 μCi/μg by the methods of Frolik et al., *J. Biol. Chem.* 259:10995–10999 (1984) and retained full biological activity as described previously (Song et al., *Endocrinology* 136:4293–4297 (1995)).

Figure 5:
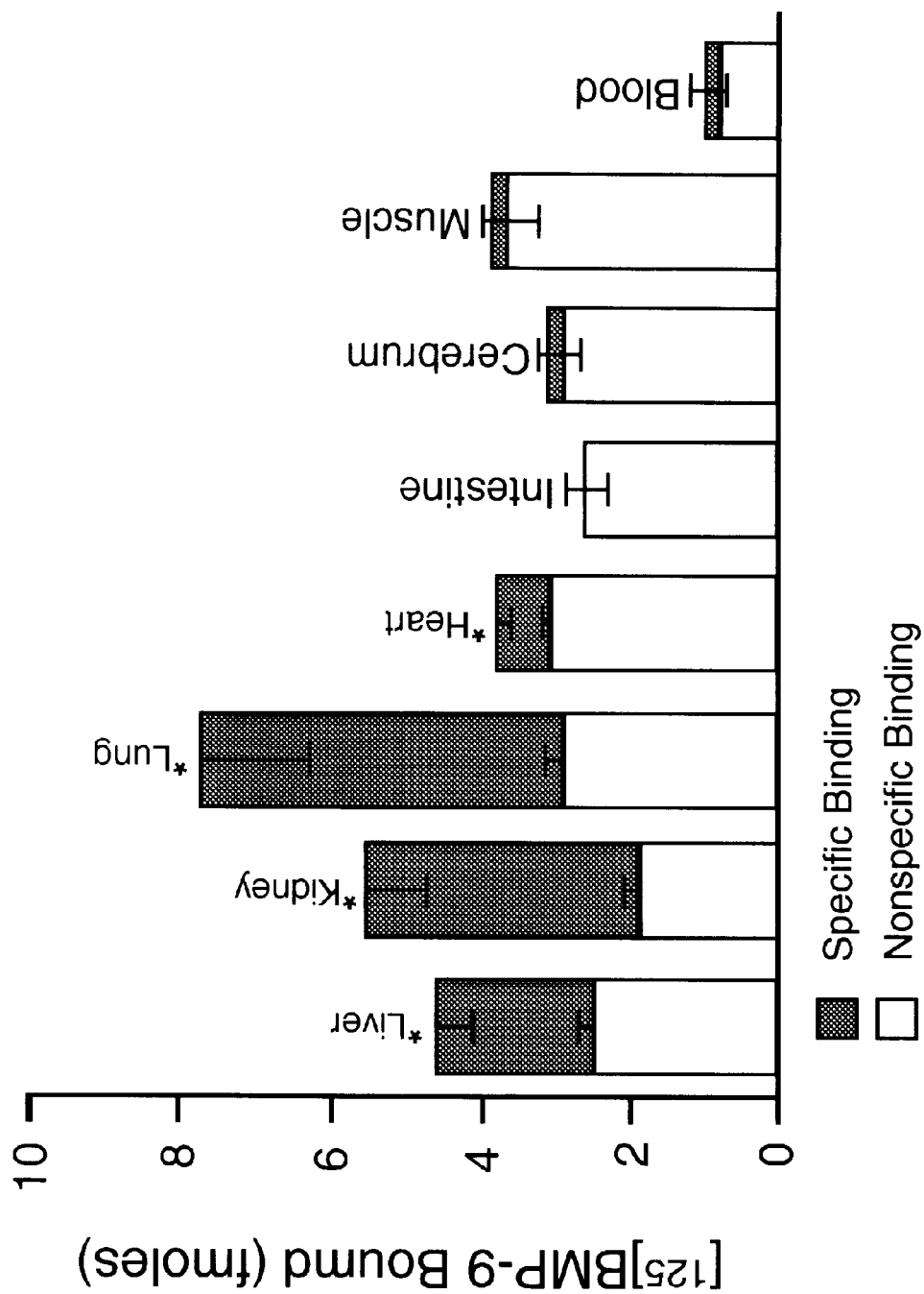
FIG. 5 sets forth results of rhBMP-9 binding to plasma membrane preparations from adult rat tissues. Specific binding was defined by the portion of [$^{125}$I]rhBMP-9 binding which was displaced with unlabeled rhBMP-9. Values are means from four or five experiments±SE *, P<0.05.

As shown in FIG. 5, [125I]rhBMP-9 binding which is displaceable by a 100-fold excess of unlabeled rhBMP-9, is evident in liver, lung, and kidney plasma membranes. To verify that this specific binding is of high affinity, a more complete displacement profile is determined with lung and kidney plasma membranes. As shown in FIG. 6, BMP-9 binding to lung and kidney plasma membranes is high affinity binding, with a Kd of 600 pM and 300 pM, respectively.

Several cell lines are tested for BMP-9 responsiveness in vitro. Cell proliferation, as indicated by [$^3$H]thymidine incorporation, is determined in cell lines derived from kidney and lung. Cell proliferation is determined by measuring [$^3$H]thymidine incorporation in subconfluent cells treated for 24 h with or without growth factors. NRK-52E (ATCC CRL 1571), WI-38 (ATCC CCL-75), CCD-11Lu (ATCC CCL-202), CCD-16Lu (ATCC CCL-204), and A-549 (ATCC CCL-185) cell lines are placed at 10$^4$ cells/well in 96 well plates and assayed for [$^3$H]thymidine incorporation as described above. IMCD-3 cells (ATCC #CRL-2123) are cultured in a collagen matrix as described by Barros et al., *PNAS USA* 92:4412–4416 (1995), and treated with growth factors for 6 days to allow tubule formation.

Figure 7:
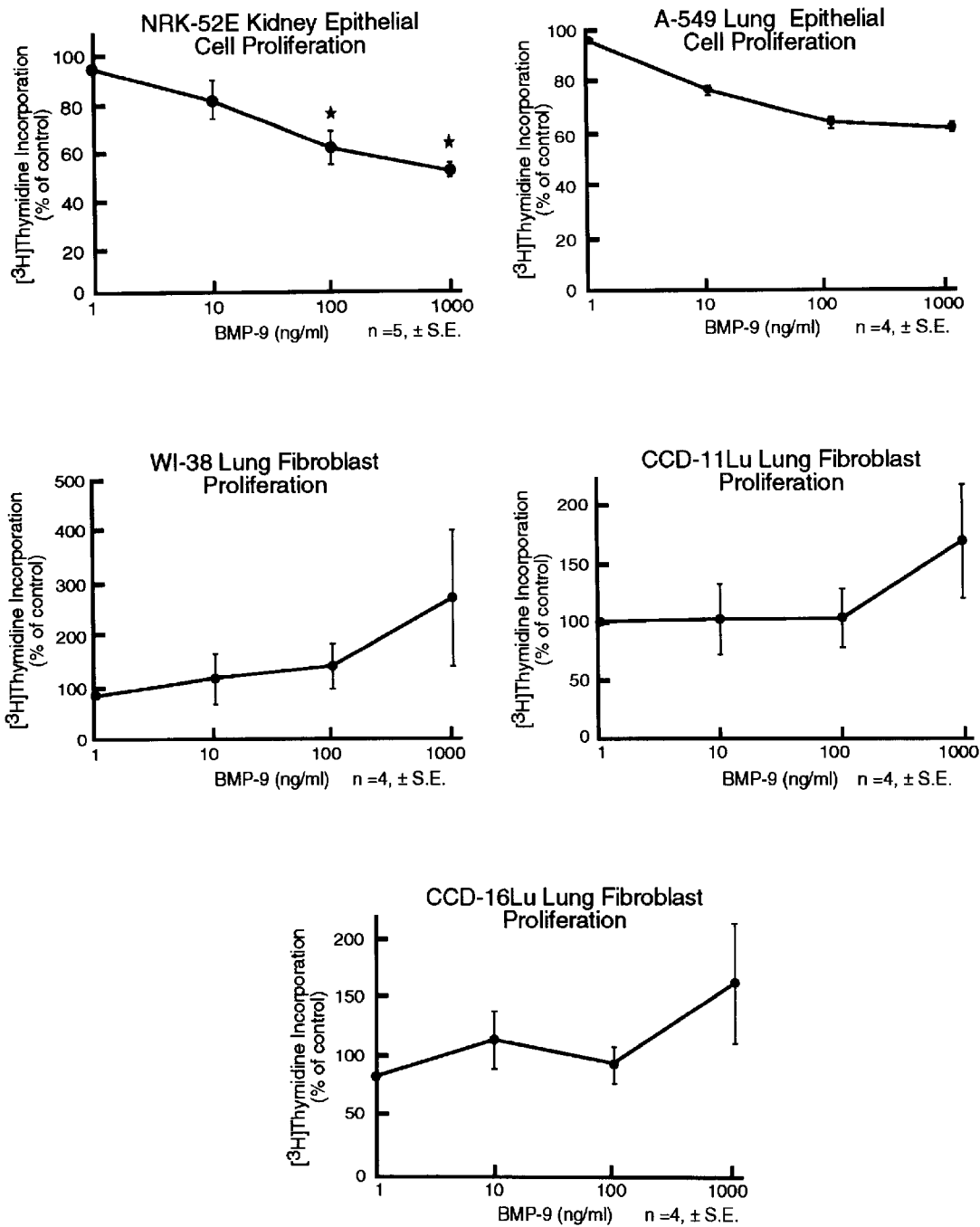
FIG. 7 sets forth effects of rhBMP-9 on kidney and lung cell proliferation. Values are means of three experiments±SE *, P<0.05.

As shown in FIG. 7, rhBMP-9 inhibited proliferation in A-549 (ATCC CCL-185) lung epithelial cells and NRK-52E (ATCC CRL-1571) kidney epithelial cells. In contrast, BMP-9 appeared to stimulate proliferation in several fibroblast cell lines derived from lung. A statistically significant stimulation is evident in WI-38 cells at high doses of rhBMP-9. A similar rhBMP-9-induced stimulation is also observed in CCD-11Lu and CCD-16Lu lung fibroblasts. The effect of rhBMP-9 on tubulogenesis was examined in IMCD-3 cells, another epithelial kidney cell line. These cells have been shown to form tubules when cultured in a 3-dimensional collagen gel in the presence of HGF [Barros et al., *PNAS USA* 92:4412–4416 (1995)]. As shown in FIG. 8, the cells constitutively form condensations under serum-free conditions, with occasional nonbranching tubulogenesis. rhHGF treatment (100 ng/ml) for 6 days induced a marked branching tubulogenesis, as has been reported previously. In contrast, rhBMP-9 treatment (100 ng/ml) did not induce tubules and inhibited the cell condensations and tubule formation observed under control conditions. These results demonstrate responsiveness to BMP-9 in kidney cells as well. It is therefore contemplated that both lung and kidney cells are physiological targets for BMP-9.

EXAMPLE X
Expression Pattern of BMP-9

Figure 9:
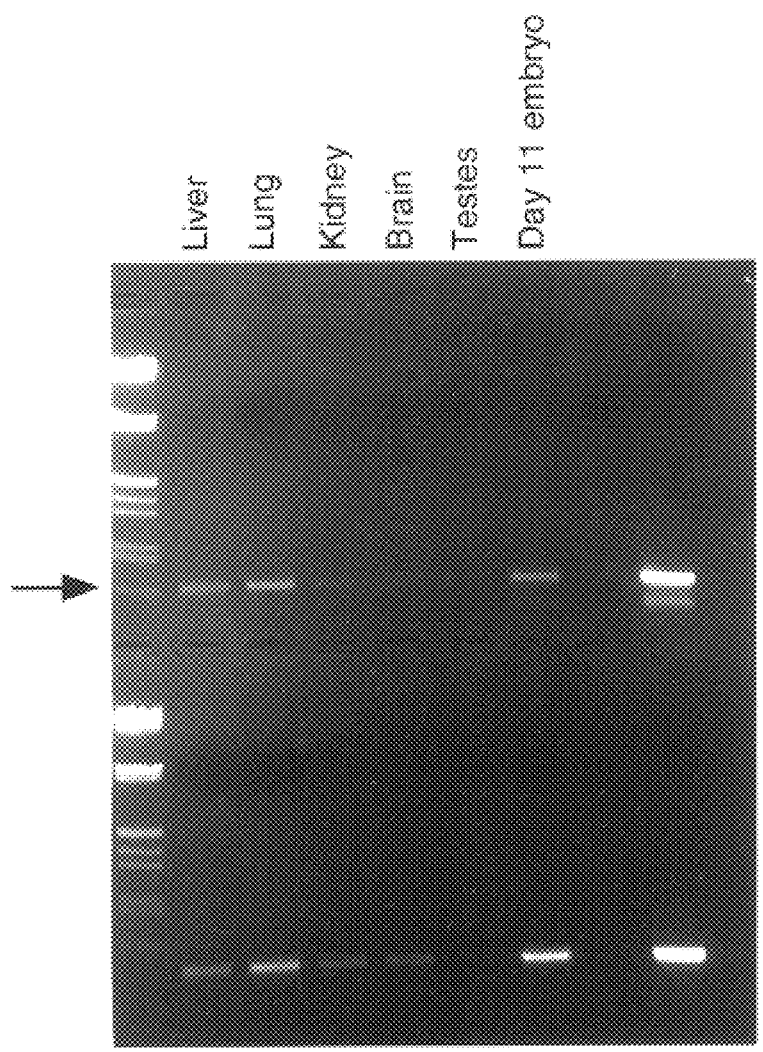
FIG. 9 sets forth BMP-9 expression in adult mouse tissues. Southern blot is representative of two independent PCR analyses.

The expression pattern of BMP-9 was determined in the adult mouse. Single strand cDNA is prepared from adult mouse tissues and used as a template for PCR analysis. First strand cDNA is prepared from 1 μg of poly(A+) -RNA from different adult mouse tissues using the cDNA Cycle Kit (Invitrogen, San Diego, Calif.), 10% of the total cDNA is used as a template in the first PCR reaction. The primers are from the murine BMP-9 sequence (SEQ ID NO:1), AGATG-GATACACAGCTGTGG (SEQ ID NO:1) and TTCTAC-CCACTAACCCTTCC (SEQ ID NO:1). This PCR reaction is used as a template for a second PCR reaction with a nested primer pair from the murine BMP-9 sequence (SEQ ID NO:1), TGCACCCAAGGAATATGACG (SEQ ID NO:1), CCAGTCATTGTCACTTCAGC (SEQ ID NO:1). The conditions for both PCR reactions are 30 cycles of 1.5 min at 94° C., 2 min at 60° C. and 2 min at 72° C., preceded by heating to 94° C. for 3 min. The PCR reaction products are analyzed by electrophoresis on a 1% agarose gel and photographed. The DNA is transferred to nylon membranes which are prehybridized with 50% formamide, 0.1% SDS, 2×SSc, 50 μg/ml herring sperm DNA and 1× Denhardt's at 42° C. for 1 h. Hybridization with random primed full length murine BMP-9 probe is performed with the same conditions for 16 h. Filters are washed to the stringency of 0.1×SSC, 0.1% SDS at 65° C. This analysis reveals that amplified DNA from adult mouse liver, lung, kidney, brain, heart and testes were all found to hybridize to a murine BMP-9 probe (FIG. 9). This finding, together with the results of the plasma membrane binding experiments, suggest that BMP-9 acts on lung and kidney cells as a paracrine or autocrine factor.

EXAMPLE XI

Using Northern analysis, BMP-9 and BMP-9-related proteins can be tested for their effects on various cell lines. Suitable cell lines include cell lines derived from E13 mouse limb buds. After 10 days of treatment with BMP-9 or BMP-9-related protein, the cell phenotype is examined histologically for indications of tissue differentiation. In addition, Northern analysis of mRNA from BMP-9 or BMP-9-related protein treated cells can be performed for various markers including one or more of the following markers for bone, cartilage and/or tendon/ligament, as described in Table IV:

TABLE IV

| Marker | Bone | Cartilage | Tendon/Ligament |
|---|---|---|---|
| Osteocalcin | + | − | − |
| Alkaline Phosphatase | + | − | − |
| Proteoglycan Core Protein | ±[1] | + | ±[2] |
| Collagen Type I | + | + | + |
| Collagen Type II | ±[1] | + | ±[2] |
| Decorin | + | + | + |
| Elastin | ±[3] | ? | + |

[1]Marker seen early, marker not seen as mature bone tissue forms
[2]Marker depends upon site of tendon; strongest at bone interface
[3]Marker seen at low levels

EXAMPLE XII

Embryonic Stem Cell Assay

In order to assay the effects of the BMP-9 proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A method for decreasing proliferation of kidney epithelial cells in a patient in need of same comprising the step of administering an amount of a BMP-9 protein encoded by a DNA sequence comprising a sequence selected from the group consisting of:
   (a) nucleotides 124 through 453 of SEQ ID NO: 8;
   (b) nucleotides 145 through 453 of SEQ ID NO: 8;
   (c) nucleotides 610 through 1893 of SEQ ID NO: 1;
   (d) nucleotides 628 through 1893 of SEQ ID NO: 1;
   (e) nucleotides encoding amino acids 1 or 8 through 110 of SEQ ID NO: 9; and
   (f) nucleotides encoding amino acids 1 or 8 through 110 of SEQ ID NO: 2 effective for decreasing proliferation of kidney epithelial cells to said patient.

2. A method for decreasing proliferation of lung epithelial cells in a patient in need of same comprising the step of administering an amount of a BMP-9 protein encoded by a DNA sequence comprising a sequence selected from the group consisting of:
   (a) nucleotides 124 through 453 of SEQ ID NO: 8;
   (b) nucleotides 145 through 453 of SEQ ID NO: 8;
   (c) nucleotides 610 through 1893 of SEQ ID NO: 1;
   (d) nucleotides 628 through 1893 of SEQ ID NO: 1;
   (e) nucleotides encoding amino acids 1 or 8 through 110 of SEQ ID NO: 9; and
   (f) nucleotides encoding amino acids 1 or 8 through 110 of SEQ ID NO: 2 effective for decreasing the proliferation of ling epithelial cells to said patient.

3. A method for inhibiting kidney tubule formation in a patient in need of same comprising the step of administering an amount a BMP-9 protein encoded by a DNA sequence comprising a sequence selected from the group consisting of:
   (a) nucleotides 124 through 453 of SEQ ID NO: 8;
   (b) nucleotides 145 through 453 of SEQ ID NO: 8;
   (c) nucleotides 610 through 1893 of SEQ ID NO: 1;
   (d) nucleotides 628 through 1893 of SEQ ID NO: 1;
   (e) nucleotides encoding amino acids 1 or 8 through 110 of SEQ ID NO: 9; and
   (f) nucleotides encoding amino acids 1 or 8 through 110 of SEQ ID NO: 2 effective for inhibiting kidney tubule formation to said patient.

* * * * *